US012007393B2

(12) United States Patent
Serra Elizalde et al.

(10) Patent No.: US 12,007,393 B2
(45) Date of Patent: Jun. 11, 2024

(54) METHODS BASED ON THE DETECTION OF RAD51 FOCI IN TUMOR CELLS

(71) Applicants: Fundació Privada Institut D'Investigació Oncològica De Vall Hebron, Barcelona (ES); Astrazeneca UK Limited, Cambridge (GB); Xentech SAS, Evry (FR)

(72) Inventors: Violeta Serra Elizalde, Barcelona (ES); Judith Balmaña Gelpi, Barcelona (ES); Cristina Cruz Zambrano, Barcelona (ES); Alba Llop Guevara, Barcelona (ES); Marta Castroviejo Bermejo, Logroño (ES); Mark J. O'Connor, Little Chesterford (GB); Gemma Nicole Jones, Little Chesterford (GB)

(73) Assignees: FUNDACIÓ PRIVADA INSTITUT D'INVESTIGACIÓ ONCÒLOGICA DE VALL HEBRON, Barcelona (ES); ASTRAZENECA UK LIMITED, Cambridge (GB); XENTECH SAS, Evry (FR)

( * ) Notice: Subject to any disclaimer, the term of this patent is extended or adjusted under 35 U.S.C. 154(b) by 744 days.

(21) Appl. No.: 16/956,112

(22) PCT Filed: Dec. 21, 2018

(86) PCT No.: PCT/EP2018/086759
§ 371 (c)(1),
(2) Date: Jun. 19, 2020

(87) PCT Pub. No.: WO2019/122411
PCT Pub. Date: Jun. 27, 2019

(65) Prior Publication Data
US 2020/0319182 A1 Oct. 8, 2020

(30) Foreign Application Priority Data
Dec. 21, 2017 (EP) ..................... 17382884

(51) Int. Cl.
| | | |
|---|---|---|
| *G01N 33/574* | (2006.01) | |
| *A61K 31/166* | (2006.01) | |
| *A61K 31/407* | (2006.01) | |
| *A61K 31/4184* | (2006.01) | |
| *A61K 31/454* | (2006.01) | |
| *A61K 31/5025* | (2006.01) | |
| *A61K 31/55* | (2006.01) | |
| *A61K 31/551* | (2006.01) | |
| *A61P 35/00* | (2006.01) | |
| *G01N 33/50* | (2006.01) | |

(52) U.S. Cl.
CPC ......... *G01N 33/574* (2013.01); *A61K 31/166* (2013.01); *A61K 31/407* (2013.01); *A61K 31/4184* (2013.01); *A61K 31/454* (2013.01); *A61K 31/5025* (2013.01); *A61K 31/55* (2013.01); *A61K 31/551* (2013.01); *A61P 35/00* (2018.01); *G01N 33/5091* (2013.01); *G01N 33/5748* (2013.01); *G01N 2333/916* (2013.01); *G01N 2800/52* (2013.01)

(58) Field of Classification Search
CPC ............. G01N 33/574; G01N 33/5091; G01N 33/5748; G01N 2333/916
See application file for complete search history.

(56) References Cited

U.S. PATENT DOCUMENTS

| | | |
|---|---|---|
| 2011/0288080 A1 | 11/2011 | Swamy |
| 2013/0210779 A1 | 8/2013 | Gonzalo et al. |
| 2014/0257659 A1 | 9/2014 | Dariush |
| 2016/0296633 A1 | 10/2016 | Goldenberg et al. |
| 2017/0209594 A1 | 7/2017 | Goldenberg et al. |

FOREIGN PATENT DOCUMENTS

| | | |
|---|---|---|
| WO | WO 2008/066624 A1 | 6/2008 |
| WO | WO 2010/082821 A1 | 7/2010 |

OTHER PUBLICATIONS

Alhilli, M. M. et al. "In vivo anti-tumor activity of the PARP inhibitor niraparib in homologous recombination deficient and proficient ovarian carcinoma," Gynecologic Oncology, 2016, vol. 143(2), pp. 379-388, AcademicPress, London, GB.
Brill, E. et al. "Prexasertib, a cell cycle checkpoint kinases 1 and 2 inhibitor, increases in vitro toxicity of PARP inhibition by preventing Rad51 foci formation in BRCA wild type high-grade serous ovarian cancer," Oncotarget 2017, vol. 8(67), pp. 111026-111040.
Cruz C. et al. "RAD51 foci as a functional biomarker of homologous recombination repair and PARP inhibitor resistance in germline BRCA-mutated breast cancer," Annals of Oncology, 2018, vol. 29(5), pp. 1203-1210.
Database EMBASE, database accession No. EMB-618663886.
Fong, P. C. et al. "Inhibition of Poly(ADP-Ribose) Polymerase in Tumors from BRCA Mutation Carriers," N Engl J Med, 2009, vol. 361, pp. 123-134.

(Continued)

*Primary Examiner* — Mark Halvorson
*Assistant Examiner* — Dennis J Sullivan
(74) *Attorney, Agent, or Firm* — Gary J. Gershik

(57) ABSTRACT

The invention provides a method allowing to determine whether a subject diagnosed with cancer is sensitive or resistant to an anti-cancer treatment, based on the level of cells with RAD51 foci in a sample containing tumor cells isolated from said subject, wherein the subject has not received at 24 hours prior to the isolation of the sample, a chemotherapy selected from the group consisting of AC, FEC, ECF and navelbine/epirubicin, and wherein the sample has not been treated with a method that induces DNA damage before determining the level of cells with RAD51 foci.

7 Claims, 14 Drawing Sheets

(56) References Cited

OTHER PUBLICATIONS

Graeser, M. et al. "A Marker of Homologous Recombination Predicts Pathologic Complete Response to Neoadjuvant Chemotherapy in Primary Breast Cancer," Clinical Cancer Research, 2010, vol. 16, pp. 6159-6168.
International Search Report dated Jan. 28, 2019 in connection with PCT International Application No. PCT/EP2018/086759.
Ivashkevich, A. et al. "Use of the γ-H2AX assay to monitor DNA damage and repair in translational cancer research," Cancer Lett, 2012, vol. 327(1-2), pp. 123-133.
Kochupurakkal, B. S. et al. "Development of a RAD51-based assay for determining homologous recombination proficiency and PARP inhibitor sensitivity," AACR Annual Meeting 2017, Apr. 1-5, 2017; Washington, DC, Abstract 2796.
Lang, F. et al. "CTCF prevents genomic instability by promoting homologous recombination-directed DNA double-strand break repair," Proc Natl Acad Sci USA, 2017, vol. 114, pp. 10912-10917.
Liu, Y. et al., "RAD51 Mediates Resistance of Cancer Stem Cells to PARP Inhibition in Triple-Negative Breast Cancer," Clinical Cancer Research 2017, vol. 23(2), pp. 514-2.
Moudry, P. et al. "TOP BP1 regulates RAD51 phosphorylation and chromatin loading and determines PARP inhibitor sensitivity," Journal of Cell Biology, 2016, vol. 212(3), pp. 281-288.
Mueck, K. et al. "Akt1 Stimulates Homologous Recombination Repair of DNA Double-Strand Breaks in a Rad51-Dependent Manner," Int J Mol Sci, 2017, vol. 18, p. 2473.
Mukhopadhyay, A. et al. "Development of a Functional Assay for Homologous Recombination Status in Primary Cultures of Epithelial Ovarian Tumor and Correlation with Sensitivity to Poly(ADP-Ribose) Polymerase Inhibitors," Clinical Cancer Research, 2010, vol. 16(8) , pp. 2344-2351.
Naipal, K. A. T. et al. "Functional Ex Vivo Assay to Select Homologous Recombination-Deficient Breast Tumors for PARP Inhibitor Treatment," Clin Cancer Res, 2014, vol. 20, pp. 4816-4826.
Patel, D. S. et al. "BLM helicase regulates DNA repair by counteracting RAD51 loading at DNA double-strand break sites," J Cell Biol, 2017, vol. 216, pp. 3521-3534.
Philip, C. et al. "Inhibition of PI3K-AKT-mTOR pathway sensitizes endometrial cancer cell lines to PARP inhibitors," BMC Cancer, 2017, vol. 17, p. 638.
Schultz, N. et al. "Poly (ADP-ribose) polymerase (PARP-1) has a controlling role in homologous recombination," Nucleic Acids Research 2003, vol. 31(17) , pp. 4959-4964.
Stover, E. H. et al. "Biomarkers of Response and Resistance to DNA Repair Targeted Therapies," Clin Cancer Res, 2016, vol. 22, pp. 5651-5660.
Tsvetkova, A. et al. "γH2AX, 53BP1 and Rad51 protein foci changes in mesenchymal stem cells during prolonged X-ray irradiation," Oncotarget, 2017, vol. 8, pp. 64317-64329.
Vierstraete, J. et al. "Accurate quantification of homologous recombination in zebrafish: brca2 deficiency as a paradigm," Sci Rep, 2017, vol. 7, pp. 1-10.
Wang, X. and David T. Weaver "The ups and downs of DNA repair biomarkers for PARP inhibitor therapies," Am J Cancer Res, 2011, vol. 1, pp. 301-327.
Willers, H. et al. "DNA Damage Response Assessments in Human Tumor Samples Provide Functional Biomarkers of Radiosensitivity," Semin Radiat Oncol, 2015, vol. 25, pp. 237-250.
Written Opinion of the International Searching Authority dated Jan. 28, 2019 in connection with PCT International Application No. PCT/EP2018/086759.
Yazinski, S. A. et al. "ATR inhibition disrupts rewired homologous recombination and fork protection pathways in PARP inhibitor resistant BRCA-deficient cancer cells," Genes and Development, 2017, vol. 31, pp. 1-15.
Yin, K. et al. "NR4A2 Promotes DNA Double-strand Break Repair Upon Exposure to UVR," Mol Cancer Res, 2017, vol. 15, pp. 1184-1196.
Shah, M. M. et al., "An ex vivo assay of XRT-induced Rad51 foci formation predicts response to PARP-inhibition in ovarian cancer", Gynecologic oncology, 2014, vol. 134.2, pp. 331-337.
Abida, W et al., "Rucaparib in Men with Metastatic Castration-Resistant Prostate Cancer Harboring a BRCA1 or BRCA2 Gene Alteration", Aug. 14, 2020, 38(32): 3763-3771.
Blanc-Durand, F et al., "A RAD51 functional assay as a candidate test for homologous recombination deficiency in ovarian cancer" Jan. 20, 2023, 171; 106-113.
Byrski, T et al., "Response to neoadjuvant therapy with cisplatin in BRCA1-positive breast cancer patients", Jul. 23, 2008, 115; 359-363.
Byrski, T et al., "Results of a phase II open-label, non-randomized trial of cisplatin chemotherapy in patients with BRCA1-positive metastatic breast cancer" Jul. 20, 2012, 14; R110, 1-8.
Carreira, A et al., "Biomarkers Associating with PARP Inhibitor Benefit in Prostate Cancer in the TOPARP-B Trial" Nov. 2021, 2812-2827.
Cass, I et al., "Improved Survival in Women with BRCA-Associated Ovarian Carcinoma" May 1, 2003, 97(9): 2187-2195.
Compadre, A et al., "RAD51 Foci as a Biomarker Predictive of Platinum Chemotherapy Response in Ovarian Cancer" Apr. 25, 2023; OF1-OF14.
Coussy, F et al., "BRCAness, SLFN11, and RB1 loss predict response to topoisomerase I inhibitors in triple-negative breast cancers" Feb. 19, 2020, 1-25.
Cruz, C et al., "RAD51 foci as a functional biomarker of homologous recombination repair and PARP inhibitor resistance in germline BRCA-mutated breast cancer" Apr. 4, 2018, 29(5); 1203-1210.
De Bono, J et al., "Olaparib for Metastatic Castration-Resistant Prostate Cancer" May 28, 2020, 382(22); 2091-2102.
Domchek, S et al., "Efficacy and safety of olaparib monotherapy in germline BRCA1/2 mutation carriers with advanced ovarian cancer and three or more lines of prior therapy" Feb. 2016, 1-14.
Golan, T et al., "Maintenance Olaparib for Germline BRCA-Mutated Metastatic Pancreatic Cancer" Jun. 2, 2019, 381(4); 317-327.
Kaye, S et al., "Phase II, Open-Label, Randomized, Multicenter Study Comparing the Efficacy and Safety of Olaparib, a Poly (ADP-Ribose) Polymerase Inhibitor, and Pegylated Liposomal Doxorubicin in Patients With BRCA1 or BRCA2 Mutations and Recurrent Ovarian Cancer" Feb. 1, 2012, 30(4); 372-379.
Kristeleit, R et al., "A Phase I-II Study of the Oral PARP Inhibitor Rucaparib in Patients with Germline BRCA1/2-Mutated Ovarian Carcinoma or Other Solid Tumors" Aug. 1, 2017, 23(15); 4095-4106.
Litton, J et al., "Talazoparib in Patients with Advanced Breast Cancer and a Germline BRCA Mutation" Aug. 23, 2018, 379(8); 753-763.
Llop-Guevara, A et al., "Association of RAD51 with homologous recombination deficiency (HRD) and clinical outcomes in untreated triple-negative breast cancer (TNBC): analysis of the GeparSixto randomized clinical trial" Sep. 11, 2021, 32(12); 1590-1596.
Mateo, J et al., "Olaparib in patients with metastatic castration-resistant prostate cancer with DNA repair gene aberrations (TOPARP-B): a multicentre, open-label, randomised, phase 2 trial" Jan. 2020, 21; 162-174.
Pellegrino, B et al., "Preclinical In Vivo Validation of the RAD51 Test for Identification of Homologous Recombination-Deficient Tumors and Patient Stratification" Apr. 15, 2022, 82(8); 1646-1657.
Robson, M et al., "Olaparib for Metastatic Breast Cancer in Patients with a Germline BRCA Mutation" Jun. 4, 2017, 377(6); 523-533.
Swisher, E et al., "Rucaparib in relapsed, platinum-sensitive high-grade ovarian carcinoma (ARIEL2 Part 1): an international, multicentre, open-label, phase 2 trial" 2017, 1-39.
Tan, D et al., ""BRCAness" Syndrome in Ovarian Cancer: A Case-Control Study Describing the Clinical Features and Outcome of Patients With Epithelial Ovarian Cancer Associated With BRCA1 and BRCA2 Mutations" Dec. 1, 2008, 26(34); 5530-5536.

(56) References Cited

OTHER PUBLICATIONS

Wohlschlegel, J.A., et al., 2022 American Journal of Pathology, 161:267-273.
Darzynkiewicz, Z. et al. 2015, Oncotarget, 6:11735-11750.

A

B

METHODS BASED ON THE DETECTION OF RAD51 FOCI IN TUMOR CELLS

RELATED APPLICATIONS

This application is a § 371 national stage of PCT International Application No. PCT/EP2018/086759, filed Dec. 21, 2018, claiming priority of European Patent Application No. 17382884.9, filed Dec. 21, 2017, the contents of each of which are hereby incorporated by reference into this application.

FIELD OF THE INVENTION

The present invention relates to methods for predicting and monitoring the response of a subject diagnosed with cancer to an anti-cancer treatment, for selecting a customized therapy for the subject, for classifying the subject into a patient cohort, and for predicting whether the tumor of the subject is capable of DNA repair by the homologous recombination repair (HRR) pathway. Said methods are based on the presence of RAD51 foci in a sample comprising tumor cells from the subject, without the need of exposing the sample to any method inducing DNA damage before the analysis of the sample. It further relates to the use of kits in said methods, and to medicaments used in the treatments referred in the methods.

BACKGROUND ART

Cells are constantly exposed to a variety of conditions that induce DNA damage, including genotoxic stresses from cell metabolism and the environment. A vast number of DNA lesions may form that confer toxicities and mutagenesis if not repaired, such as DNA single-strand breaks (SSBs) and double-strand breaks (DSBs). To maintain genome integrity, DNA is repaired using different DNA repair pathways. In the simplest terms, they consist of ligating the broken DNA ends together to repair SSBs or on using templating recombination from the homologous DNA strand respectively to repair DSBs. Additionally, the network of DNA damage response (DDR) also confers alternative or backup mechanisms means for DNA repair, making it difficult to predict repair capability from genetic deficiencies alone.

Deficiency in DNA repair genes has been associated with high susceptibility to cancer. A well-studied case is the deficiency in the activity of the BRCA proteins. BRCA1 and BRCA2 (BRCA1/2) proteins have an important role in the repair of DNA DSBs by the HRR pathway. The BRCA1-PALB2-BRCA2 protein complex facilitates the localization of RAD51 to the DNA DSB, forming nuclear RAD51 aggregates (i.e. foci) and mediating strand invasion and homologous repair. Thus, a lack of function of BRCA1 and BRCA2 in tumor cells results in a deficient repair of DNA DSBs mediated by RAD51 that has been associated with genetically inherited breast cancer.

Anti-cancer therapies have been designed to specifically target tumor cells with such deficiencies in the DDR, such as those based on PARP inhibitors (PARPi). PARP protein is activated in response to DNA SSB by detecting and binding to SSBs to initiate DNA repair. Activated PARP then recruits other DNA repair proteins to facilitate the DNA repair. PARP inhibition causes an increase in persistent SSBs in DNA that are converted into DSBs. HRR deficient cells such as cells lacking BRCA1/2 are unable to repair the accumulated DSBs caused by PARP inhibition, resulting in collapsed replication forks, chromosome instability and cell death. Thus, BRCA1/2 mutant cells were identified as especially sensitive to PARP inhibitors. However, not all patients with cancer characterized by BRCA1/2 mutations respond to PARPi therapy, and are thus considered PARPi resistant. The mechanisms underlying said resistance have been studied to improve the treatment of said patients and for predicting tumor response before administration of the treatment.

For instance, it has been shown that BRCA1/2 reversion mutations, or so-called secondary mutations, cause recovery of HRR function and resistance to PARP inhibition. Similarly, loss of 53BP1 drives resistance to PARPi in BRCA1 deficient tumors. A method has been proposed to identify tumors with deficient HRR. Said method consists on analyzing the formation of RAD51 nuclear foci in a post-chemotherapy tumor biopsy or an ex vivo irradiated tumor sample.

However, there is a need in the art of alternative and simpler methods allowing the differentiation between HRR-proficient and deficient tumors to classify patients with and without resistance to anti-cancer therapies, such as therapies based on PARPi.

SUMMARY OF THE INVENTION

In a first aspect, the invention relates to a method for predicting the response of a subject diagnosed with cancer to an anti-cancer treatment, comprising:
  i) determining the level of cells with RAD51 foci in a sample containing tumor cells isolated from said subject wherein the subject has not received, at 24 hours prior to the isolation of the sample, a chemotherapy selected from the group consisting of AC, FEC, ECF and navelbine/epirubicin, and wherein the sample has not been treated with a method that induces DNA damage before determining the level of cells with RAD51 foci, and
  ii) comparing the level obtained in step i) with a reference value, wherein:
    a level of cells with RAD51 foci lower than said reference value indicates that the subject is predicted to respond to the anti-cancer treatment, or
    a level of cells with RAD51 foci equal or higher than said reference value indicates that the subject is predicted not to respond to the anti-cancer treatment.

In a second aspect, the invention relates to a method for selecting a customized therapy for a subject diagnosed with cancer, comprising:
  i) determining the level of cells with RAD51 foci in a sample containing tumor cells isolated from said subject, wherein the subject has not received, at 24 hours prior to the isolation of the sample, a chemotherapy selected from the group consisting of AC, FEC, ECF and navelbine/epirubicin, and wherein the sample has not been treated with a method that induces DNA damage before determining the level of cells with RAD51 foci, and
  ii) comparing the level obtained in step i) with a reference value, wherein:
    a level of cells with RAD51 foci lower than said reference value indicates that the therapy to be selected comprises agents specific to treat tumors with DNA damage response deficiencies, or
    a level of cells with RAD51 foci equal or higher than said reference value indicates that the therapy to be selected does not comprise agents specific to treat tumors with DNA damage response deficiencies.

In a third aspect, the invention relates to a method for classifying a subject diagnosed with cancer into a patient cohort, comprising:
i) determining the level of cells with RAD51 foci in a sample containing tumor cells isolated from said subject wherein the subject has not received, at 24 hours prior to the isolation of the sample, a chemotherapy selected from the group consisting of AC, FEC, ECF and navelbine/epirubicin, and wherein the sample has not been treated with a method that induces DNA damage before determining the level of cells with RAD51 foci, and
ii) comparing the level obtained in step i) with a reference value, wherein:
a patient is classified into a cohort characterized by responding to an anti-cancer treatment if the level of cells with RAD51 foci is lower than said reference value, or
a patient is classified into a cohort characterized by not responding to an anti-cancer treatment if the level of cells with RAD51 foci is higher than said reference value.

In a fourth aspect, the invention relates to a method for predicting whether a tumor from a subject diagnosed with cancer is capable of DNA repair by homologous recombination repair:
i) determining the level of cells with RAD51 foci in a tumor sample, wherein the tumor has been isolated from a subject that has not received, at 24 hours prior to the isolation of the tumor, a chemotherapy selected from the group consisting of AC, FEC, ECF and navelbine/epirubicin, and wherein the sample has not been treated with a method that induces DNA damage before determining the level of cells with RAD51 foci, and
ii) comparing the level obtained in step i) with a reference value, wherein:
a level of cells with RAD51 foci lower than said reference value is indicative that the tumor is capable of DNA repair by homologous recombination, or
a level of cells with RAD51 foci equal or higher than said reference value is indicative that the tumor is not capable of DNA repair by homologous recombination mediated.

In a fifth aspect, the invention relates to a medicament for use in the treatment of a cancer in a subject, wherein the subject has been identified as responder to said medicament by the method as defined in the first aspect of the invention.

In a sixth aspect, the invention relates to a medicament for use in the treatment of a cancer in a subject, wherein the treatment has been designed by a method as defined in the second aspect of the invention.

In a seventh aspect, the invention relates to a use of a kit in a method referred in any of the first, second, third or fourth aspect of the invention, wherein the kit comprises an antibody that is capable of specifically recognizing the RAD51 protein.

BRIEF DESCRIPTION OF THE DRAWINGS

FIG. 1 shows the anti-tumor activity of the PARP inhibitor (PARPi) olaparib in patient-derived tumor xenografts (PDXs). In particular, 6 PDXs exhibit a complete response (CR), 2 PDXs a partial response (PR), 2 PDX a stable disease (SD) and 34 a progressive disease (PD). The panel entitles 39 PDX models of breast cancer (BrC), 3 PDX models of high-grade serous ovarian cancer (HGSOC or OvC) and 2 PDX derived from pancreatic cancer (PaC). The waterfall plot represents the percentage of tumor volume change compared to the tumor volume at treatment initiation. The table underneath summarizes the characteristics of each PDX model, including the presence or not of a germline BRCA1/2 mutation (gBRCA), the presence or not of an homologous recombination repair (HRR) alteration (of genetic or epigenetic origin) and the cancer type/subtype. Filled squares in black indicate positivity for that trait. Of note, neither gBRCA1/2 mutations nor HRR alterations predicted the response to the PARPi olaparib. 20%, −30% and −95% change from baseline are marked by doted lines to indicate the range of PD, SD, PR and CR, respectively. Error bars indicate SEM from independent tumors. gBRCA, germline BRCA1/2 gene mutated; HRR alterations, tumors with alterations in HRR-related genes other than BRCA1/2, and tumors with BRCA1 promoter hypermethylation; TNBC, Triple Negative Breast Cancer; ER+BrC, Estrogen Receptor positive Breast Cancer; HGSOC or OvC, High-Grade Serous Ovarian Cancer; PaC, Pancreatic Cancer; PDX models that become olaparib resistant upon prolonged treatment are labeled with suffix OR.

DETAILED DESCRIPTION OF THE INVENTION

Figure 1:
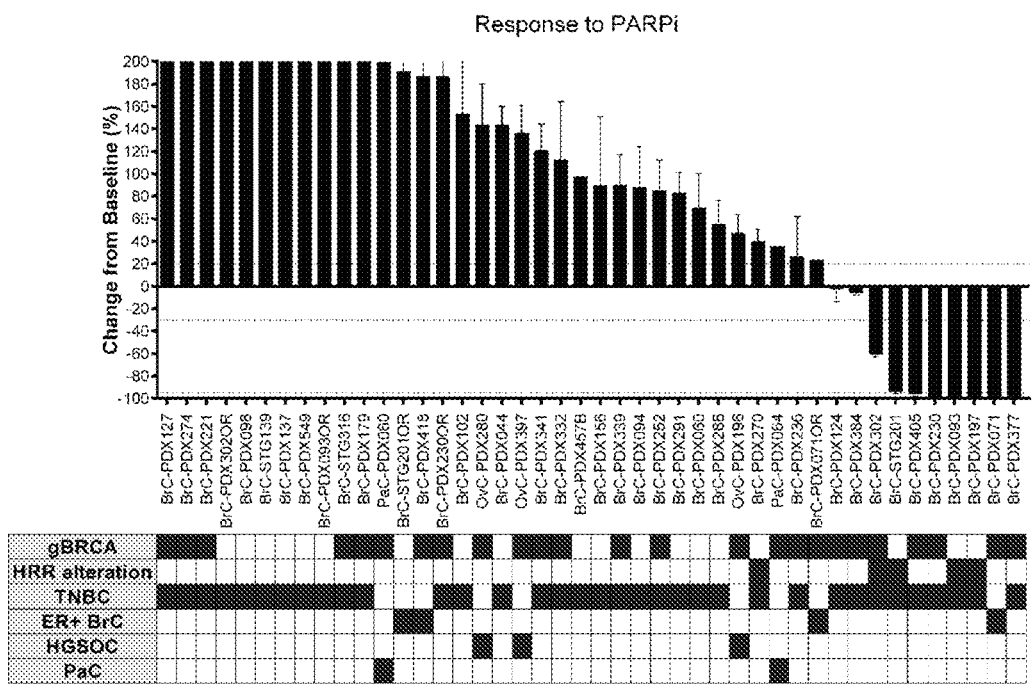

The authors of the present invention have found that the determination of the level of cells with RAD51 nuclear foci in a sample with tumor cells isolated from a subject diagnosed with cancer is related to the response of the subject to an anti-cancer treatment wherein the cells of the sample have not been exposed to a method inducing DNA damage prior to the analysis of the level of cells with RAD51 nuclear foci. Said method can be ex vivo, i.e. after isolating the tumor cells from the subject, and consists on the exposure of the sample of cells to ionizing irradiation. Additionally, the inventors have found that the method is also efficient in samples from patients not treated or treated with an anti-cancer therapy. The administration of the chemotherapy leads to the exposure of the tumor cells from the subject to the compounds of the chemotherapy, which induces DNA damage, and the subsequent rapid (within minutes) recruitment of proteins involved in DNA damage repair.

1. Methods of the Invention

A. Method for Predicting the Response of a Subject Diagnosed with Cancer to an Anti-Cancer Treatment In a first aspect, the invention relates to a method for predicting the response of a subject diagnosed with cancer to an anti-cancer treatment, comprising:
i) determining the level of cells with RAD51 foci in a sample containing tumor cells isolated from said subject wherein the subject has not received, at 24 hours prior to the isolation of the sample, a chemotherapy selected from the group consisting of AC, FEC, ECF and navelbine/epirubicin, and wherein the sample has not been treated with a method that induces DNA damage before determining the level of cells with RAD51 foci, and
ii) comparing the level obtained in step i) with a reference value, wherein:
a level of cells with RAD51 foci lower than said reference value indicates that the subject is predicted to respond to the anti-cancer treatment, or
a level of cells with RAD51 foci equal or higher than said reference value, indicates that the subject is predicted not to respond to the anti-cancer treatment.

The term "predicting the response" or "predict to respond", as used herein, refers to the probabilities by which a patient may respond to a treatment. As experts in the field will understand, and although this is not preferable, prediction does not have to be correct for 100% of the subjects who may be diagnosed or evaluated. However, the expression requires that the prediction provides correct results for a statistically significant portion of patients. Determination whether the prediction of the invention provides statistically significant results can be carried out by using standard statistical techniques such as the determination of confidence intervals, determination of p value, Student's t-test, Mann-Whitney test as described in Dowdy and Wearden, Statistics for Research, John Wiley & Sons, New York 1983. Suitable confidence intervals are at least 50%, at least 60%, at least 70%, at least 80%, at least 90%, at least 95%. P values are, preferably, 0.05, 0.001, 0.0005 or less.

The term "subject" or "patient", as used herein, refers to all animals classified as mammals and includes, but is not restricted to, domestic and farm animals, primates and humans; for example, human beings, non-human primates, cows, horses, pigs, sheep, goats, dogs, cats or rodents. Preferably, the subject is a male or female human of any age or ethnicity.

The term "diagnosed", as used herein, refers to the determination and/or identification of a disease in a subject, i.e. the opinion reached about the disease state of a subject, i.e. the diagnostic opinion. As such, it can also be regarded as an attempt to classify individuals depending on their disease condition. As it will be understood by those skilled in the art, the diagnosis of cancer, although preferred to be, need not be correct for 100% of the subjects to be diagnosed or evaluated. The term, however, requires that a statistically significant portion of subjects identified as such are suffering cancer. Whether a subject is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, or at least 95%. The p-values are, preferably, 0.05, 0.01, 0.005 or lower.

The term "cancer" refers to a group of diseases involving abnormal, uncontrolled growth and proliferation (neoplasia) of cells that form one or more malignant tumors in the subject suffering cancer, with the potential to invade or spread (metastasize) to other tissues, organs or, in general, distant parts of the organism; metastasis is one of the hallmarks of the malignancy of cancer and cancerous tumors. The term "cancer" includes, but is not restricted to, breast cancer, ovarian cancer, pancreatic cancer, prostate cancer, lung cancer, colorectal cancer, stomach/gastric cancer, endometrial/uterine/cervical cancer, bladder cancer, head and neck cancer, leukemia, cancer of the heart, of the small intestine, spleen, kidney, brain, skin, bone, bone marrow, blood, thymus, womb, testicles, hepatobiliary system and liver, sarcoma, cholangiocarcinoma, glioblastoma, multiple myeloma, lymphoma, adenoma, angiosarcoma, astrocytoma, epithelial carcinoma, germinoma, glioma, hemangioendothelioma, hemangiosarcoma, hematoma, hepatoblastoma, medulloblastoma, melanoma, neuroblastoma, hepatobiliary cancer, osteosarcoma, retinoblastoma, rhabdomyosarcoma, sarcoma and teratoma. Furthermore, this term includes acrolentiginous melanoma, actinic keratosis adenocarcinoma, adenoid cystic carcinoma, adenomas, adenosarcoma, adenosquamus carcinoma, astrocytic tumors, Bartholin gland carcinoma, basal cell carcinoma, bronchial gland carcinoma, capillary carcinoid, carcinoma, carcinosarcoma, cystadenoma, endodermal sinus tumor, endometrial hyperplasia, endometrial stromal sarcoma, endometrioid adenocarcinoma, ependymal sarcoma, Ewing sarcoma, focal nodular hyperplasia, germ cell tumors, glucagonoma, hemangioblastoma, hemagioendothelioma, hemagioma, hepatic adenoma, hepatic adenomastosis, hepatocellular carcinoma, hepatobilliary cancer, insulinoma, intraepithelial neoplasia, squamous cell intraepithelial neoplasia, invasive squamous-cell carcinoma, large cell carcinoma, leiomyosarcoma, melanoma, malignant melonoma, malignant mesothelial tumor, medulobastoma, medulloepithelioma, mucoepidermoid carcinoma, neuroblastoma, neuroepithelial adenocarcinoma, nodular melanoma, osteosarcoma, papillary serous adenocarcinoma, pituitary tumors, plasmacytoma, pseudosarcoma, pulmonary blastoma, renal cell carcinoma, retinoblastoma, rhabdomyosarcoma, serous carcinoma, microcytic carcinoma, soft tissue carcinoma, somatostatin secreting tumor, squamous carcinoma, squamous cell carcinoma, undifferentiated carcinoma, uveal melanoma, verrucous carcinoma, vipoma, Wilm tumor, intracerebral cancer, rectal cancer, astrocytoma, microcytic cancer and non-microcytic cancer, metastatic melanoma, androgen-independent metastatic prostate cancer, androgen-dependent metastatic prostate cancer. The term cancer includes both primary tumors as well as metastatic tumors.

The term "anti-cancer treatment", as used herein, refers to any treatment comprising the exposure of the subject being treated with any method used to induce death of cancerous cells. Said method is not limited to the administration of chemical agents, it can consist on surgery, chemotherapy, radiation therapy, hormonal therapy, targeted therapy including immunotherapy, or a combination thereof.

The term "surgery", when referred to cancer, refers to a major surgery where at least part of the primary tumour and/or at least part of at least one metastasis is/are removed.

The term "radiation therapy", "radiotherapy", or "ionizing radiation" as used herein, refers to a therapy using ionizing radiation, generally as part of cancer treatment to control or kill tumor cells and normally delivered by a linear accelerator. Gamma rays, X-rays, and the higher ultraviolet part of the electromagnetic spectrum are ionizing radiation, whereas the lower part of the spectrum below UV, including visible light (including nearly all types of laser light), infrared, microwaves, and radio waves are all considered non-ionizing radiation. Radiation therapy may be curative in a number of types of cancer if they are localized to one area of the body. Radiation therapy is commonly applied to the cancerous tumor because of its ability to control cell growth. Ionizing radiation works by damaging the DNA of cancerous tissue leading to cellular death.

The term "targeted therapy" as used herein refers to a therapy that blocks the growth of cancer cells by interfering with specific targeted molecules needed for carcinogenesis and tumor growth, rather than by simply interfering with all rapidly dividing cells. Because most agents for targeted therapy are biopharmaceuticals, the term biologic therapy is sometimes synonymous with targeted therapy when used in the context of cancer therapy (and thus distinguished from chemotherapy, that is, cytotoxic therapy). However, the modalities can be combined. Another form of targeted therapy involves the use of nanoengineered enzymes to bind to a tumor cell such that the body's natural cell degradation process can digest the cell, effectively eliminating it from the body. Many targeted therapies are examples of immunotherapy.

The term "immunotherapy" as used herein refers to cancer immunotherapy consisting in approaches that modify the host immune system, and/or the utilization of components of the immune system as cancer treatment. Non-limiting examples of immunotherapy include the nonspecific immune stimulants BCG and levamisole; the cytokines interferon-α and interleukin-2; the monoclonal antibodies anti-PD1, anti-PDL1, anti-CTLA-4, rituximab, ofatumumab, alemtuzumab, trastuzumab, bevacizumab, cetuximab, and panitumumab; the radiolabeled antibodies Y-90 ibritumomab tiuxetan and 1-131 tositumomab; the immunotoxin denileukin diftitox and the antibody gemtuzumab ozogamicin; nonmyeloablative allogeneic transplants with donor lymphocyte infusions; and the anti-prostate cancer cell-based therapy sipuleucel-T. Other examples of immunotherapies such as DC vaccines, CART-t cell or NK therapy. Some immunotherapies involve the removal of immune cells from the blood or from a tumor and those specific for the tumor are cultured and returned to the patient where they attack the tumor; alternatively, immune cells can be genetically engineered to express a tumor-specific receptor, cultured and returned to the patient. Cell types that can be used in this way are natural killer cells, lymphokine-activated killer cells, cytotoxic T cells and dendritic cells.

The term "chemotherapy", as used herein, is drawn to any treatment consisting in the administration of one or several anti-cancer agents, without chemical structure limitations, suitable for therapy and/or treatment of a cancer, alone or in combination with other compounds.

The expression "AC" as used herein refers to a chemotherapy consisting in the combination of two chemotherapy drugs: adriamycin/doxorubicin and cyclophosphamide.

The expression "FEC" as used herein refers to a chemotherapy consisting in the combination of three chemotherapy drugs: 5 fluorouracil (also known as 5FU), epirubicin and cyclophosphamide.

The expression "ECF" as used herein refers to a chemotherapy consisting in the combination of three chemotherapy drugs: epirubicin, cisplatin and fluorouracil.

As used herein, an "anti-cancer agent" is an agent that at least partially inhibits the development or progression of a cancer, including inhibiting in whole or in part symptoms associated with the cancer even if only for the short term. Anti-cancer agents include those used in any of the therapies described above that comprise the administration of a compound, i.e. hormonal therapy, targeted therapy, immunotherapy, chemotherapy.

Several examples of anti-cancer agents include without limitation Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Bortezomib (VELCADE); Brequinar Sodium; Bropirimine; Busulfan; Cactinomycin; Calusterone; Caracemide; Carbetimer; Carboplatin (a platinum-containing regimen); Carmustine; Carubicin Hydrochloride; Carzelesin; Cedefingol; Chlorambucil; Cirolemycin; Cisplatin (a platinum-containing regimen); Cladribine; Crisnatol Mesylate; Cyclophosphamide; Cytarabine; Dacarbazine; Dactinomycin; Daunorubicin; Decitabine; Dexormaplatin; Dezaguanine; Diaziquone; Docetaxel (TAXOTERE); Doxorubicin; Pegylated liposomal Doxorubicin; Droloxifene; Dromostanolone; Duazomycin; Edatrexate; Eflornithine; Elsamitrucin; Enloplatin; Enpromate; Epipropidine; Epirubicin; Erbulozole; Erlotinib (TARCEVA), Esorubicin; Estramustine; Etanidazole; Etoposide; Etoprine; Fadrozole; Fazarabine; Fenretinide; Floxuridine; Fludarabine; 5-Fluorouracil; Flurocitabine; Fosquidone; Fostriecin; Gefitinib (IRESSA), Gemcitabine; Hydroxyurea; Idarubicin; Ifosfamide; Ilmofosine; Imatinib mesylate (GLEEVEC); Interferon alpha-2a; Interferon alpha-2b; Interferon alpha-nl; Interferon alpha-n3; Interferon beta-I a; Interferon gamma-I b; Iproplatin; Irinotecan; Lanreotide; Lenalidomide (REVLLMID, REVIMID); Letrozole; Leuprolide; Liarozole; Lometrexol; Lomustine; Losoxantrone; Masoprocol; Maytansine; Mechlorethamine; Megestrol; Melengestrol; Melphalan; Menogaril; Mercaptopurine; Methotrexate; Metoprine; Meturedepa; Mitindomide; Mitocarcin; Mitocromin; Mitogillin; Mitomalcin; Mitomycin; Mitosper; Mitotane; Mitoxantrone; Mycophenolic Acid; Nocodazole; Nogalamycin; Ormaplatin; Oxisuran; Paclitaxel; Pemetrexed (ALIMTA), Pegaspargase; Peliomycin; Pentamustine; Pentomone; Peplomycin; Perfosfamide; Pipobroman; Piposulfan; Piritrexim Isethionate; Piroxantrone; Plicamycin; Plomestane; Porfimer; Porfiromycin; Prednimustine; Procarbazine; Puromycin; Pyrazofurin; Riboprine; Rogletimide; Safingol; Semustine; Simtrazene; Sitogluside; Sparfosate; Sparsomycin; Spirogermanium; Spiromustine; Spiroplatin; Streptonigrin; Streptozocin; Sulofenur; Talisomycin; Tamsulosin; Taxol; Taxotere; Tecogalan; Tegafur; Teloxantrone; Temoporfin; Temozolomide (TEMODAR); Teniposide; Teroxirone; Testolactone; Thalidomide (THALOMID) and derivatives thereof; Thiamiprine; Thioguanine; Thiotepa; Tiazofurin; Tirapazamine; Topotecan; Toremifene; Trestolone; Triciribine; Trimetrexate; Triptorelin; Tubulozole; Uracil; Mustard; Uredepa; Vapreotide; Verteporfin; Vinblastine; Vincristine; Vindesine; Vinepidine; Vinglycinate; Vinleurosine; Vinorelbine; Vinrosidine; Vinzolidine; Vorozole; Zeniplatin; Zinostatin; Zorubicin.

The anti-cancer agent may also be an enzyme inhibitor including without limitation tyrosine kinase inhibitor, a CDK inhibitor, a MAP kinase inhibitor, or an EGFR inhibitor. The tyrosine kinase inhibitor may be without limitation Genistein (4', 5, 7-trihydroxyisoflavone), Tyrphostin 25 (3,4, 5-trihydroxyphenyl), methylene]-propanedinitrile, Herbimycin A, Daidzein (4',7-dihydroxyisoflavone), AG-126, trans-1-(3'-carboxy-4'-hydroxyphenyl)-2-(2",5"-dihydroxyphenyl)ethane, or HDBA (2-Hydroxy5-(2,5-Dihydroxybenzylamino)-2-hydroxybenzoic acid. The CDK inhibitor may be without limitation p21, p27, p57, p15, p16, p18, or p19. The MAP kinase inhibitor may be without limitation KY12420 (C23H2408), CNI-1493, PD98059, or 4-(4-Fluorophenyl)-2-(4-methylsulfinyl phenyl)-5-(4-pyridyl) 1H-imidazole. The EGFR inhibitor may be without limitation erlotinib (TARCEVA), gefitinib (IRESSA), WHI-P97 (quinazoline derivative), LFM-A12 (leflunomide metabolite analog), ABX-EGF, lapatinib, canertinib, ZD-6474 (ZACTIMA), AEE788, and AG1458.

Additionally, several anti-cancer agents can be categorized as DNA damaging agents and these include agents that induce DNA damage directly and agents that indirectly induce DNA damage by targeting a protein involved in the DNA damage response of the cell resulting in an increase in the amount of DNA damage in the cell. Agents that induce DNA damage directly can be: DNA alkylating agents (e.g., cyclophosphamide, dacarbazine, procarbazine, carmustine, lomustine, ifosfamide, melphalan, busulfan, thiotepa), DNA alkylating-like agents (e.g., carboplatin, cisplatin), DNA strand break inducing agents (e.g., bleomycin, doxorubicin, daunorubicin, idarubicin, mitomycin C), anti-metabolic agents (e.g., cytarabine, methotrexate, hydroxyurea, 5-fluorouracil, floxuridine, 6-thioguanine, 6-mercaptopurine, fludarabine, chlorodeoxyadenosine), topoisomerase inhibitors (e.g., etoposide, ramptothecin, topotecan, teniposide, mitoxantrone) or epipodophyllotoxins.

Agents that target a protein involved in the DNA damage response of the cell can be: PARP inhibitors (PARPi; e.g., olaparib, talazoparib, rucaparib, niraparib, veliparib, CEP-8983, E7016 and BGB-290), anti-microtubule agents (e.g., vincristine, vinblastine) and anthracyclines.

The term "sample" or "biological sample", as used herein, refers to biological material isolated from a subject. The biological sample contains any biological material suitable for detecting the desired protein markers. The biological sample can comprise cell and/or non-cell material of the subject. The sample can be isolated from any suitable tissue or biological fluid such as, for example blood, saliva, cerebrospinal fluid, urine, stool, bone marrow, a nipple aspirate, a solid tumor biopsy, plasma, serum, cerebrospinal liquid (CSF), feces, a buccal or buccal-pharyngeal swab, a surgical specimen, a specimen obtained from a biopsy, and a tissue sample embedded in paraffin. Methods for isolating samples are well known to those skilled in the art. In a particular embodiment, said sample comprises cancer cells, preferably breast cancer, ovarian cancer, prostate cancer, gastric cancer, pancreatic cancer, lung cancer, colorectal cancer, stomach/gastric cancer, endometrial/uterine/cervical cancer, bladder cancer, head and neck cancer, leukemia, sarcoma, cholangiocarcinoma, glioblastoma, multiple myeloma, lymphoma cells. More preferably, the sample comprises breast cancer cells, ovarian cancer cells, prostate cancer cells, gastric cancer cells or pancreatic cancer cells, even more preferably breast cancer cells, ovarian cancer cells or prostate cancer cells, yet more preferably breast cancer cells. In a preferred embodiment it is a tumor tissue sample or portion thereof. Preferably, said tumor tissue sample is a breast tumor, ovarian tumor, prostate tumor, gastric tumor, pancreatic tumor, lung tumor, colorectal tumor, stomach/gastric tumor, endometrial/uterine/cervical tumor, bladder tumor, head and neck tumor, sarcoma tumor, cholangiocarcinoma tumor, glioblastoma tumor, multiple myeloma tumor, lymphoma tumor tissue, or portion thereof, sample. More preferably, the sample is a breast tumor, ovarian tumor, prostate tumor, gastric tumor, and pancreatic tumor tissue, or portion thereof, sample; even more preferably, said sample is a breast tumor, an ovarian tumor or a prostate tumor, or portion thereof, tissue sample; yet more preferably said tumor tissue sample is a breast tumor tissue, or portion thereof, sample.

Said sample can be obtained by conventional methods, e.g., biopsy, by using methods well known to those of ordinary skilled in the related medical arts. Methods for obtaining the sample from the biopsy include gross apportioning of a mass, or microdissection or other art-known cell-separation methods. Tumor cells can additionally be obtained from fine needle aspiration cytology. In order to simplify conservation and handling of the samples, they can be a fixed tissue, paraffin embedded tissue, histological slide, cell suspension, cell pellet, cell slide, frozen solid tumor biopsy, and/or first frozen and then embedded in a cryosolidifiable medium, such as OCT-Compound, through immersion in a highly cryogenic medium that allows for rapid freeze.

The expression "DNA damage" as used herein is well-known by a skilled person in the field. It refers to an alteration in the chemical structure of DNA, such as a break in one or both strands of DNA, a base missing from the backbone of DNA, or a chemically changed base. A break in one strand of DNA is known as a single-strand break (SSB) and a break in both strands of the DNA is known as a double-strand break (DSB). DNA damage can also consist on a stalled replication fork. If not repaired by the DNA damage response machinery of the cell, DNA damage leads to accumulation of DNA damage and functional genomic alterations (i.e. genomic instability). Said alteration in the DNA can for instance provide selective advantage to the affected cell, so that it can continually proliferate and survive, leading to the formation of a tumor cell.

The expression "DNA damage response" as used herein refers to cellular pathways that monitor and repair DNA damage to maintain genomic integrity of the cell. The type of DNA damage response depends on the type of DNA damage. In general terms, it depends on whether the DNA damage consists on a SSB or in a DSB The expression "method that induces DNA damage" as used herein refers to virtually any conventional method that can be used to induce DNA damage in a sample. Virtually any conventional method can be used within the frame of the invention to induce DNA damage. For instance, a well-known method that induces DNA damage is ionizing radiation, which is a type of high-energy radiation able to re lease electrons from atoms and molecules generating ions which can break covalent bonds. Ionizing radiation directly affects DNA structure by inducing DNA breaks, particularly, DSBs. Other example of methods consist on exposing cells to oxidative stress mainly inducing DSB, methyl methane sulphonate which is an alkylation agent capable of inducing DNA lesions and subsequent SSBs and DSBs or UV light which can induce SSBs and DSBs.

The term "RAD51" as used herein refers to an enzyme with a major role in homologous recombination of DNA during DSB repair. The sequence of the protein is filed in UniProt (22 Nov. 2017) with accession number Q06609.

The term "foci" used herein refers to local accumulations of specific proteins in a site of the cell. When referring to "nuclear foci" said foci are localized in the nucleus of the cell. For instance, during DNA damage repair, DNA repair foci are formed by the local accumulations or modifications of DNA damage response proteins formed at the sites of DNA double-strand breaks. Foci can be visualized with microscopic imaging following immunostaining or fluorescent protein tagging.

The expression "reference value" refers to a laboratory value used as reference for the values/data obtained by means of samples obtained from patients. The reference value or reference level can be an absolute value, a relative value, a value that has an upper and/or lower limit, a series of values, an average value, a median, a mean value, or a value expressed by referring to a control or reference value. A reference value may be based on the value obtained from a group of patients considered to be representative, such as the values obtained in a population of subjects from a chronological age group coinciding with that of the patient object of the study or based on a set of inclusion or exclusion samples of the sample to be analyzed. Alternatively, a reference value may be based on an individual sample, such as, for example, a value obtained from a sample from the patient object of the study, but obtained at a previous point in time.

The reference value of the invention is a reference for the level of cells with RAD51 foci in the sample analyzed. The expression "level of cells" as used herein refers to an absolute value or to a relative value used to determine the amount of cells. In a preferred embodiment, the level of cells with RAD51 foci in the sample is determined as the relative level of cells with RAD51 foci with respect to:
 the number of tumor cells in the sample,
 the number of cells in the sample that are proliferating,
 the number of cells in the sample that show DNA damage, preferably double strand DNA breaks and
 the number of cells in the sample that are proliferating and that show DNA damage, preferably double strand DNA breaks.

Said relative level can be calculated as a ratio or as a percentage.

When the level of cells with RAD51 foci is calculated with respect to the number of tumor cells in the sample, the reference value expressed as percentage is at least 0.1%, at least 0.25%, at least 0.5%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15, at least 16%, at least 17%, at least 18%, at least 19%, at least 20%, wherein 100 represents the total amount of cells in the sample. In a preferred embodiment the reference value is at least 0.5%, more preferably at least 1%, yet more preferably at least 2%, even more preferably at least 5%.

When the level of cells with RAD51 foci is calculated with respect to the number of cells in the sample that are proliferating, the reference value expressed as percentage is at least 1%, at least 2%, at least 3%, at least 4%, at least 5%, at least 6%, at least 7%, at least 8%, at least 9%, at least 10%, at least 11%, at least 12%, at least 13%, at least 14%, at least 15, at least 16%, at least 17%, at least 18%, at least 19%, at least 20%, at least 21%, at least 22%, at least 23%, at least 24%, at least 25%, at least 30%, at least 35%, at least 40%, at least 45%, at least 50%, wherein 100 represents the total amount of cells in the sample that are proliferating. In a preferred embodiment the reference value is at least 1%, more preferably at least 5%, yet more preferably at least 10%, even more preferably at least 11%, even yet more preferably at least 20%.

The expression "cells ( . . . ) that are proliferating", as used herein, refers to cells in the sample that are dividing giving rise to an increase in the number of cells in the sample. Cells that are proliferating are identified by the determination of the expression of proteins involved in the division of cells. Non-limiting examples of such proteins are: Geminin, Ki-67, Proliferating cell nuclear antigen, Cyclin A2.

The term "geminin" as used herein is a nuclear protein that is absent during G1 phase and accumulates through S, G2 phase and M phases of the cell cycle. Geminin levels drop at the metaphase/anaphase transition of mitosis when it is degraded by the Anaphase Promoting Complex (APC/C).

The term "Ki-67", "MKI67" or "Antigen KI-67" as used herein refers to the Ki-67 nuclear protein which is present during all active phases of the cell cycle (G1, S, G2, and mitosis), but is absent in resting (quiescent) cells (G0). Cellular content of Ki-67 protein markedly increases during cell progression through S phase of the cell cycle.

The term "Proliferating cell nuclear antigen" or "PCNA" as used herein refers to the protein with said name, which is a DNA clamp that acts as a processivity factor for DNA polymerase 6 in eukaryotic cells and is essential for replication. PCNA is a homotrimer and achieves its processivity by encircling the DNA, where it acts as a scaffold to recruit proteins involved in DNA replication, DNA repair, chromatin remodeling and epigenetics. PCNA was originally identified as an antigen that is expressed in the nuclei of cells during the DNA synthesis phase of the cell cycle.

The term "cyclin A2" as used herein refers to the protein cyclin A2 which is expressed in dividing somatic cells. The levels of cyclin A2 are tightly synchronized with the progression of the cell cycle. Transcription initiates in late G1, peaks and plateaus in mid-S, and declines in G2.

When the level of cells with RAD51 foci is calculated with respect to the number of cells in the sample that show DNA damage, preferably double strand DNA breaks, the reference value expressed as percentage is at least 1%, at least 2%, at least 3%, at least 4%, at least 5%, at least 6%, at least 7%, at least 8%, at least 9%, at least 10%, at least 11%, at least 12%, at least 13%, at least 14%, at least 15, at least 16%, at least 17%, at least 18%, at least 19%, at least 20%, at least 21%, at least 22%, at least 23%, at least 24%, at least 25%, at least 30%, at least 35%, at least 40%, at least 45%, at least 50%, wherein 100 represents the total amount of cells in the sample that show DNA damage, preferably DSBs. In a preferred embodiment the reference value is at least 10%, even more preferably at least 16%, yet more preferably at least 17%, even more preferably at least 20%, even more preferably at least 30% even yet more preferably at least 50%.

The expression "cells ( . . . ) that show DNA damage" as used herein refers to the cells suffering DNA damage as defined above, preferably consisting in DSBs. They are identified in the sample by the determination of the expression, preferably as nuclear foci, of proteins involved in the repair of DNA damage, preferably in the repair of DSBs. Non-limiting examples of such proteins are: γH2AX, replication protein A (pRPA), p53 Binding protein 1 (53BP1), double-strand break repair protein (MRE11).

The term "γH2AX" as used herein refers to phosphorylated histone H2AX (γH2AX). It is used as a biomarker of cellular response to DSB. At the early stage after DSB formation, large numbers of γH2AX molecules form in the chromatin around the break site, creating a focus where proteins involved in DNA repair and chromatin remodeling accumulate. This amplification makes it possible to detect individual DSBs with an antibody to γH2AX.

The term "replication protein A", "pRPA" or "RPA" refers to the protein with said name, which is the major protein that binds to single-stranded DNA (ssDNA) in eukaryotic cells. During DNA replication, RPA prevents single-stranded DNA (ssDNA) from winding back on itself or from forming secondary structures. This keeps DNA unwound for the polymerase to replicate it. RPA also binds to ssDNA during the initial phase of homologous recombination to repair DSBs. Like its role in DNA replication, binding of RPA keeps ssDNA from binding to itself (self-complementizing) so that the resulting nucleoprotein filament can then be bound by RAD51 and its cofactors. RPA also binds to DNA during the nucleotide excision repair process. This binding stabilizes the repair complex during the repair process. A bacterial homolog is called single-strand binding protein (SSB).

The term "p53 Binding protein 1" or "53BP1" as used herein refers to a protein that functions in the DNA double-strand break repair pathway choice, promoting non-homologous end joining (NHEJ) pathways, and limiting homologous recombination. This protein plays multiple roles in the DNA damage response, including promoting checkpoint signaling following DNA damage, acting as a scaffold for recruitment of DNA damage response proteins to damaged chromatin, and promoting NHEJ pathways by limiting end resection following a double-strand break. These roles are also important during V(D)J recombination, class switch recombination and at unprotected telomeres. Alternative splicing results in multiple transcript variants encoding different isoforms.

The term "double-strand break repair protein" or "MRE11" as used herein refers to a protein part of the MRN complex, which plays a central role in double-strand break (DSB) repair, DNA recombination, maintenance of telomere integrity and meiosis. The complex possesses single-strand endonuclease activity and double-strand-specific 3'-5' exonuclease activity, which are provided by MRE11. RAD50 may be required to bind DNA ends and hold them in close proximity. This could facilitate searches for short or long regions of sequence homology in the recombining DNA templates, and may also stimulate the activity of DNA ligases and/or restrict the nuclease activity of MRE11 to prevent nucleolytic degradation past a given point. The complex may also be required for DNA damage signaling via activation of the ATM kinase.

When the level of cells with RAD51 foci is calculated with respect to the number of cells in the sample that are proliferating and that show DNA damage, preferably double strand DNA breaks, the reference value expressed as percentage is at least 1%, at least 2%, at least 3%, at least 4%, at least 5%, at least 6%, at least 7%, at least 8%, at least 9%, at least 10%, at least 11%, at least 12%, at least 13%, at least 14%, at least 15, at least 16%, at least 17%, at least 18%, at least 19%, at least 20%, at least 21%, at least 22%, at least 23%, at least 24%, at least 25%, at least 30%, at least 35%, at least 40%, at least 45%, at least 50%, at least 60%, at least 70%, at least 75%, at least 80%, at least 90%, at least 95%, wherein 100 represents the total amount of cells that are proliferating and that also show DNA damage, preferably DSBs. In a preferred embodiment the reference value is at least 5%, more preferably at least 10%, even more preferably it is at least 20%, even more preferably at least 30%, yet even more preferably at least 50%.

The expression "to respond to the anti-cancer treatment" as used herein, refers to a favorable response to the anti-cancer treatment, which is understood by a skilled person as the stabilization or reduction of the size of the tumor/s and/or of the number of tumors in the patient and/or the inhibition of a metastatic process. In this case, a skilled person would also refer to the patient as "sensitive to the anti-cancer treatment". On the contrary, if the response is not favorable as just indicated, a skilled person would also refer to the patient as "resistant to the anti-cancer treatment". Said response can be determined by at least one criteria selected from the group consisting of clinical benefit rate, overall survival, progression free survival, disease free survival, pathologic complete response, clinical complete remission, clinical partial remission, clinical stable disease, recurrence, survival without metastasis, decrease in circulating tumor cells, response of circulating markers and RECIST criteria for tumor response assessment. The moment after the initiation of therapy in which the response is evaluated is no particularly limited. Thus, response to therapy can be determined at least 1, 2, 3, 4, 5, 6, 7, 8 9, 10 or 11 months after the initiation of the first therapy or at least 1, 2, 3, 4, 5, 6, 7, 8, 9, 10 or more years after the initiation of the first therapy. In addition, the type and number of lines of therapies applied to the patient before the determination of the response is also not particularly limited. Thus, the response can be determined in patients after the patient has been treated with a first line of therapy including surgical therapy, chemotherapy or surgery in combination with adjuvant or neoadjuvant chemotherapy or any type of therapy, or after the patient has been treated with two or more sequential or simultaneous lines of therapy.

The expression "clinical benefit rate", as used herein refers to the percentage of patients with cancer who have shown an improvement in at least one important symptom or element of the quality of life that directly results from a treatment, without any decline in any other element of the patient's quality of life. Said improvement is understood as a complete remission, partial remission or a stabilization of the disease.

The expression "overall survival" as used herein refers to the length of time from either the date of diagnosis or the start of treatment for a disease, such as cancer, that patients diagnosed with the disease are still alive.

The expression "progression free survival" as used herein refers to the length of time during and after the treatment of a disease, such as cancer, that a patient lives with the disease but it does not get worse.

The expression "disease free survival" as used herein refers to the length of time after primary treatment for a cancer ends that the patient survives without any signs or symptoms of that cancer.

The expression "pathologic complete response" as used herein refers to the absence of residual invasive tumor cells after administration of an anti-cancer treatment.

The expression "clinical complete remission" as used herein refers to the disappearance of all signs of cancer in response to treatment.

The expression "clinical partial remission" as used herein refers to a decrease in the size of a tumor, or in the extent of cancer in the body, in response to treatment.

The expression "clinical stable disease" as used herein refers to a cancer that is neither decreasing nor increasing in extent or severity.

The term "recurrence" as used herein refers to the appearance of cancer after treatment and after a period of time during which cancer was not detected.

The expression "survival without metastasis" as used herein refers to the length of time after treatment for a cancer ends that the patient survives without any signs or symptoms of cancer metastasis.

The expression "decrease in circulating tumor cells" as used herein refers to a decrease in the concentration of circulating tumor cells in the blood or in the lymph of a patient with metastatic cancer. A decrease in circulating tumor cells is associated with efficacy of a therapy against the metastatic cancer.

The expression "response of circulating markers" as used herein refers to the variation on the concentration in blood or in the lymph of proteins or nucleic acids associated with a specific cancer after treatment against said specific cancer.

The term "RECIST" as used herein refers to the "Response Evaluation Criteria In Solid Tumors". It is a standard way to measure how well a cancer patient responds to treatment. It is based on whether tumors shrink, stay the same, or get bigger. To use RECIST, there must be at least one tumor that can be measured on x-rays, computed tomography (CT) scans, or magnetic resonance imaging (MRI) scans. The types of response a patient can have are a complete response (CR), a partial response (PR), progressive disease (PD), and stable disease (SD). In the preclinical studies with murine xenograft models, we apply the RECIST criteria on tumors measured with a caliper.

B. Method for Selecting a Customized Therapy for a Subject Diagnosed with Cancer In a second aspect, the invention relates to a method for selecting a customized therapy for a subject diagnosed with cancer, comprising:
  i) determining the level of cells with RAD51 foci in a sample containing tumor cells isolated from said subject, wherein the subject has not received, at 24 hours prior to the isolation of the sample, a chemotherapy selected from the group consisting of AC, FEC, ECF and navelbine/epirubicin, and wherein the sample has not been treated with a method that induces DNA damage before determining the level of cells with RAD51 foci, and
  ii) comparing the level obtained in step i) with a reference value,
  wherein:
    a level of cells with RAD51 foci lower than said reference value indicates that the therapy to be selected comprises agents specific to treat tumors with DNA damage response deficiencies, or
    a level of cells with RAD51 foci equal or higher than said reference value indicates that the therapy to be selected does not comprise agents specific to treat tumors with DNA damage response deficiencies.

The term "selecting a customized therapy" or "selecting a personalized therapy" as used herein refers to selecting appropriate and optimal therapies based on a patient's specific medical characteristics, resulting from its personal genetic background. In the context of the present invention, said characteristic is specific of the tumor cells of the patient, and consists on the level of cells with RAD51 foci in a sample comprising tumor cells isolated from the patient, wherein the subject has not received, at 24 hours prior to the isolation of the sample, chemotherapy selected from the group consisting of AC, FEC, ECF and navelbine/epirubicin, and wherein the sample has not been treated with a method that induces DNA damage before determining the level of cells with RAD51 foci. Said level of cells with RAD51 foci and reference value are determined as indicated in section 1-A.

In the context of the present invention, the therapy to be selected or not selected is a therapy comprising agents specific to treat tumors with DNA damage response deficiencies.

The expression "tumors with DNA damage response deficiencies" or "tumor cells with DNA damage response deficiencies", or "tumor cells characterized by a loss of function of at least one protein involved in the DNA damage response of the cell" as used herein, refers to malignant tumors formed by tumor cells wherein the DNA damage response is altered. Said alteration may consist on the presence of increased DNA damage (compared to non-tumor cells obtained from the same organ tissue and subject as the tumor cells), tumor-specific DNA repair defects, and a failure to stop or to stall the cell cycle before the damaged DNA is passed on to daughter cells, or in a combination thereof. Any of these alterations can result from the abnormal expression of a protein involved in the DNA damage response. Non-limiting examples of said proteins are ATM, ATR, BRCA 1, BRCA2, BP53, P53, CDC25, CHK1, CHK2, NBS, MRE1J, RAD51, PALB2, PARP or a combination thereof. Said alterations lead to the genomic instability characteristic of cancerous or malignant tumor cells.

The term "ATR" as used herein refers to the Serine/threonine-protein kinase ATR also known as the ataxia telangiectasia and Rad3-related protein (ATR) or the FRAP-related protein 1 (FRP1). ATR is a serine/threonine-specific protein kinase that is involved in sensing DNA damage and activating the DNA damage checkpoint, leading to cell cycle arrest. ATR is activated in response to persistent single-stranded DNA, which is a common intermediate formed during DNA damage detection and repair. Single-stranded DNA occurs at stalled replication forks and as an intermediate in DNA repair pathways such as nucleotide excision repair and homologous recombination repair. ATR works with a partner protein called ATRIP to recognize single-stranded DNA coated with RPA. Once ATR is activated, it phosphorylates Chk1, initiating a signal transduction cascade that culminates in cell cycle arrest. In addition to its role in activating the DNA damage checkpoint, ATR is thought to function in unperturbed DNA replication. ATR is related to a second checkpoint-activating kinase, ATM.

The term "ATM" as used herein refers to ATM serine/threonine kinase. The ATM gene codes for a 350 kDa protein consisting of 3056 amino acids. ATM belongs to the superfamily of phosphatidylinositol 3-kinase-related kinases (PIKKs). The protein ATM is a serine/threonine protein kinase that is recruited and activated by DNA double-strand breaks. It phosphorylates several key proteins that initiate activation of the DNA damage checkpoint, leading to cell cycle arrest, DNA repair or apoptosis. A complex of the three proteins MRE11, RAD50 and NBS1 (XRS2 in yeast), called the MRN complex in humans, recruits ATM to double strand breaks (DSBs) and holds the two ends together. ATM directly interacts with the NBS1 subunit and phosphorylates the histone variant H2AX on Ser139. This phosphorylation generates binding sites for adaptor proteins with a BRCT domain. These adaptor proteins then recruit different factors including the effector protein kinase CHK2 and the tumor suppressor p53. The effector kinase CHK2 is phosphorylated and thereby activated by ATM. Activated CHK2 phosphorylates phosphatase CDC25A, which is degraded thereupon and can no longer dephosphorylate CDK2-Cyclin, resulting in cell-cycle arrest. If the DSB cannot be repaired during this rapid response, ATM additionally phosphorylates MDM2 and p53 at Ser15. p53 is also phosphorylated by the effector kinase CHK2. These phosphorylation events lead to stabilization and activation of p53 and subsequent transcription of numerous p53 target genes including CDK inhibitor p21 which lead to long-term cell-cycle arrest or even apoptosis.

The terms "BRCA1" and "BRCA2" as used herein refer to the proteins called "breast cancer 1" and "breast cancer 2" respectively. They are also referred to as "breast cancer susceptibility proteins". They are involved in the repair of chromosomal damage with an important role in the error-free repair of DNA double strand breaks. If BRCA1 or BRCA2 itself is damaged by a BRCA mutation in cells from the breast, damaged DNA is not repaired properly, and this increases the risk for breast cancer. Although the structures of the BRCA1 and BRCA2 genes are very different, at least some functions are interrelated.

BRCA2 is involved in double-strand break repair and/or homologous recombination. It acts by targeting RAD51 to ssDNA over double-stranded DNA which stimulates strand invasion during homologous recombination. The localization of RAD51 to the DNA double-strand break requires the formation of BRCA1-PALB2-BRCA2 complex.

BRCA1 appears to play a role in two distinct pathways for double strand break repair, non-homologous end joining and homology-directed repair. Thus, BRCA1 interacts with proteins involved in both the non-homologous end joining pathway (including the Mre11, Rad50, Nbs1 complex) and homologous repair (RAD51 and BRCA2, among others).

The term "Cdc25" as used herein refers to the Cdc25 phosphatases (Cdc25A, B, and C), which are responsible for removing the inhibitory phosphates from Thr-14 and Tyr-15 in cyclin-dependent kinases which activates the kinases and drives the progression through the cell cycle. While DNA repair is under way, mitosis should be prevented, and thus the DNA damage response activates a cell-cycle checkpoint to prevent mitoses. Two protein kinases, Chk1 and Cds1, can enforce this checkpoint by phosphorylating the mitotic inducer Cdc25 thus preventing entry into mitosis.

The term "Chk1" as used herein refers to the "checkpoint kinase 1", which is a Serine/threonine-specific protein kinase. Activation of Chk1 results in the initiation of cell cycle checkpoints, cell cycle arrest, DNA repair and cell death to prevent damaged cells from progressing through the cell cycle. Chk1 is regulated by ATR through phosphorylation, forming the ATR-Chk1 pathway. This pathway recognizes single strand DNA (ssDNA). Often ssDNA can be a result of abnormal replication during S phase through the uncoupling of replication enzymes helicase and DNA polymerase. These ssDNA structures attract ATR and eventually activates the checkpoint pathway.

However, activation of Chk1 is not solely dependent on ATR, intermediate proteins involved in DNA replication are often necessary. Regulatory proteins such as replication protein A, Claspin, Tim/Tipin, Rad 17, TopBP1 may be involved to facilitate Chk1 activation. Additional protein interactions are involved to induce maximal phosphorylation of Chk1. Chk1 activation can also be ATR-independent through interactions with other protein kinases such as PKB/AKT, MAPKAPK and p90/RSK.

The term "Chk2" as used herein refers to the "checkpoint kinase 2". Chk2 regulates cell division. When DNA undergoes a double-stand break, Chk2 protein is activated. More specifically, ATM phosphorylates site Thr68 and activates Chk2 Once activated Chk2 phosphorylates downstream targets including CDC25 phosphatases, responsible for dephosphorylating and activating the cyclin-dependent kinases (CDKs). Thus, Chk2's inhibition of the CDC25 phosphatases prevents entry of the cell into mitosis, similarly to Chk1. Furthermore, the Chk2 protein interacts with several other proteins including p53 (p53). Stabilization of p53 by Chk2 leads to cell cycle arrest in phase G1. Furthermore, Chk2 is known to phosphorylate the cell-cycle transcription factor E2F1 and the promyelocytic leukemia protein (PML) involved in apoptosis (programmed cell death).

The term "NBS1" as used herein refers to the protein encoded by the gene causing the "Nijmegen breakage syndrome". NBS1 typically forms a complex with the hMRE11/hRAD50 nuclease and functions in homologous recombination repair for DNA double-strand breaks (DSBs). The interactions of NBS1 with ATM, MDC1, γH2AX, and TopBP1 are important for focus formation at the sites of DSB and the activation of the ATM/ATR-dependent cell cycle checkpoint following DNA damage.

The term "PALB2" as used herein refers to the "partner and localizer of BRCA2". This protein binds to and colocalizes with BRCA2 in nuclear foci and likely permits the stable intranuclear localization and accumulation of BRCA2. PALB2 binds the single strand DNA and directly interacts with the recombinase RAD51 to stimulate strand invasion, which is a vital step of homologous recombination.

The term "PARP" as used herein refers to the "Poly (ADP-ribose) polymerase". The PARP family comprises 17 members they all have very different structures and functions in the cell. The main role of PARP is to detect SSB and initiate the SSB repair by signaling the enzymatic machinery involved in said SSB repair, mainly in BER pathway. Once PARP detects a SSB, it binds to the DNA, undergoes a structural change, and begins the synthesis of a polymeric adenosine diphosphate ribose (poly (ADP-ribose) or PAR) chain, which acts as a signal for the other DNA-repairing enzymes. Target enzymes include DNA ligase III (LigIII), DNA polymerase beta (polβ), and scaffolding proteins such as X-ray cross-complementing gene 1 (XRCC1). After repairing, the PAR chains are degraded via Poly (ADP-ribose) glycohydrolase (PARG).

The rest of terms in the context of the present method of the invention have the meaning defined for the previous method.

C. Method for Classifying a Subject with Cancer into a Patient Cohort

In a third aspect, the invention relates to a method for classifying a subject with cancer into a patient cohort, comprising:
i) determining the level of cells with RAD51 foci in a sample containing tumor cells isolated from said subject wherein the subject has not received, at 24 hours prior to the isolation of the sample, a chemotherapy selected from the group consisting of AC, FEC, ECF and navelbine/epirubicin, and wherein the sample has not been treated with a method that induces DNA damage before determining the level of cells with RAD51 foci, and
ii) comparing the level obtained in step i) with a reference value, wherein:
a patient is classified into a cohort characterized by responding to an anti-cancer treatment if the level of cells with RAD51 foci is lower than said reference value, or
a patient is classified into a cohort characterized by not responding to an anti-cancer treatment if the level of cells with RAD51 foci is higher than said reference value.

The term "cohort" or "patient cohort" as used herein, refers to a group of subjects affected by common diseases, environmental or temporal influences, treatments, or other traits whose progress is assessed in a research or clinical study. In the present invention the subjects of all cohorts are diagnosed with cancer, and the trait common for all the subjects within a cohort is the positive or negative response (depending on the cohort) to an anti-cancer treatment. Said response of each subject is determined by comparing the level of cells with RAD51 foci with a reference value in a sample containing tumor cells isolated from said subject wherein the subject has not received, at 24 hours prior to the isolation of the sample, a chemotherapy selected from the group consisting of AC, FEC, ECF and navelbine/epirubicin, and wherein the sample has not been treated with a method that induces DNA damage before determining the level of cells with RAD51 foci. Said level of cells with RAD51 foci and reference value are determined as indicated in section 1-A.

The rest of terms in the context of the present method of the invention also have the meaning defined for the previous methods.

D. Method for Predicting Whether a Tumor from a Subject is Capable of DNA Repair by Homologous Recombination In a fourth aspect, the invention relates to a method for predicting whether a tumor from a subject is capable of DNA repair by homologous recombination comprising:
i) determining the level of cells with RAD51 foci in a tumor sample, wherein the tumor has been isolated from a subject that has not received, at 24 hours prior to the isolation of the tumor, a chemotherapy selected from the group consisting of AC, FEC, ECF and navelbine/epirubicin, and wherein the sample has not been treated with a method that induces DNA damage before determining the level of cells with RAD51 foci, and
ii) comparing the level obtained in step i) with a reference value, wherein:
a level of cells with RAD51 foci lower than said reference value is indicative that the tumor is capable of DNA repair by homologous recombination, or
a level of cells with RAD51 foci equal or higher than said reference value is indicative that the tumor is not capable of DNA repair by homologous recombination.

The expression "predicting whether a tumor from a subject diagnosed with cancer is capable of DNA repair by homologous recombination", as used herein, refers to the probabilities by which a tumor from a subject patient may be capable of DNA repair by homologous recombination. As experts in the field will understand, and although this is not preferable, prediction does not have to be correct for 100% of the tumors from subjects analyzed. However, the expression requires that the prediction provides correct results for a statistically significant portion of patients. Determination whether the prediction of the invention provides statistically significant results can be carried out by using standard statistical techniques such as the determination of confidence intervals, determination of p value, Student's t-test, Mann-Whitney test as described in Dowdy and Wearden, Statistics for Research, John Wiley & Sons, New York 1983. Suitable confidence intervals are at least 50%, at least 60%, at least 70%, at least 80%, at least 90%, at least 95%. p values are, preferably, 0.2, 0.1, 0.05.

The term "probability", as used herein, is understood as indicated in section 1-A.

The expression "homologous recombination repair", or "HRR" as used herein, refers to a homologous recombination process occurring as DDR in a cell to principally repair DSBs. In general terms, HRR requires the presence of an identical or nearly identical sequence to be used as a template for repair of the break. The enzymatic machinery responsible for this repair process is nearly identical to the machinery responsible for chromosomal crossover during meiosis. This pathway allows a damaged chromosome to be repaired using a sister chromatid (available in G2 after DNA replication) or a homologous chromosome as a template.

Thus, the method disclosed in this section D allows distinguishing between patients with cancers wherein HRR is proficient/functional or deficient/non-functional.

The rest of terms used in the definition of the present method of the invention have been explained in respect to the previous methods of the invention and are equally applicable to the present method.

E. Preferred Embodiments of the Methods of the Invention

In a preferred embodiment, in the method defined in any of the previous aspects of the invention a cell is defined as having RAD51 foci if it contains at least one, at least 2, at least 3, at least 4, at least 5, at least 6, at least 7, at least 8, at least 9, at least 10, at least 12, at least 15 at least 20 RAD51 foci in the nucleus. In a more preferred embodiment, said cell should contain at least 1 RAD51 foci in the nucleus. In an even more preferred embodiment, said cell should contain at least 5 RAD51 foci in the nucleus.

In another preferred embodiment, the RAD51 foci are identified with an immunoassay using an antibody that is capable of specifically recognizing the RAD51 protein. The term "immunoassay" as used herein refers to a biochemical test that measures the presence or concentration of a molecule in a solution through the use of an antibody or an antigen-binding fragment thereof. The molecule detected by the immunoassay is often referred to as an "analyte" and is in many cases a protein, although it may be other kinds of molecules, of different size and types, as long as the proper antibodies that have the adequate properties for the assay are developed. Immunoassays employ a variety of different labels to allow for detection of antibodies or an antigen-binding fragment thereof. Labels are typically chemically linked or conjugated to the desired antibody or antigen-binding fragment thereof.

Common labels to use in immunoassays are enzymes. Common immunoassays which employ enzymes are enzyme-linked immunosorbent assays (ELISAs), or sometimes enzyme immunoassays (EIAs).

Enzymes used in immunoassays as labels include horseradish peroxidase (HRP), alkaline phosphatase (AP) or glucose oxidase. These enzymes allow for detection often because they produce an observable color change in the presence of certain reagents. In some cases these enzymes are exposed to reagents which cause them to produce light or chemiluminescence.

Radioactive isotopes can be incorporated into immunoassay reagents to produce a radioimmunoassay (RIA). Radioactivity emitted by bound antibody-antigen complexes can be easily detected using conventional methods.

Fluorogenic reporters like phycoerythrin are used in a number of modern immunoassays. Protein microarrays are a type of immunoassay that often employ fluorogenic reporters.

While labels are generally employed in immunoassays, there are certain type of assays that do not rely on labels, but instead employ detection methods that don't require the modification or labeling the components of the assay. Surface plasmon resonance is an example of technique that can detect binding between an unlabeled antibody and antigens. It consists on the resonant oscillation of conduction electrons at the interface between negative and positive permittivity material stimulated by incident light. Another demonstrated label-less immunoassay involves measuring the change in resistance on an electrode as antigen binds to it.

Said principles of the immunoassay techniques are used by a skilled person to determine the expression and/or the formation of foci of the protein of interest at a single cell level. Methods allowing said determination are known by a skilled person. Non-limiting examples of such methods are immunohistochemistry, immunofluorescence, immune-electron microscopy or flow-cytometry.

The term "immunohistochemistry" as used herein refers to a technique that involves the process of selectively imaging antigens (e.g. proteins) in cells of a tissue section, or of a sample of cells, by exploiting the principle of the immunoassays described above. Visualization of the antibodies bound to the cells analyzed involves the use of a microscope such as an electron microscope (EM). Immunohistochemistry can be used on tissue sections, cultured cell lines, or individual cells, and may be used to analyze the distribution of proteins, glycans, and small biological and non-biological molecules within the cells or more generally within the sample of cells.

Preparation of the sample is critical to maintain cell morphology, tissue architecture and the antigenicity of target epitopes. This requires proper tissue collection, fixation and sectioning. A solution of paraformaldehyde is often used to fix tissue, but other methods may be used. The tissue may then be sliced or used whole, dependent upon the purpose of the experiment or the tissue itself. Before sectioning, the tissue sample may be embedded in a medium, like paraffin wax or cryomedia. Sections can be sliced on a variety of instruments, most commonly a microtome, cryostat, or compresstome tissue slicer. Specimens are typically sliced at a range of 3 µm-50 µm. The slices are then mounted on slides, dehydrated using alcohol washes of increasing concentrations (e.g., 50%, 75%, 90%, 95%, 100%), and cleared using a detergent like xylene before being imaged under a microscope. Depending on the method of fixation and tissue preservation, the sample may require additional steps to make the epitopes available for antibody binding, including deparaffinization and antigen retrieval. For formalin-fixed paraffin-embedded tissues, antigen-retrieval is often necessary, and involves pre-treating the sections with heat or protease. These steps may make the difference between the target antigens staining or not staining.

The term "immunofluorescene" as used herein, refers to a specific example of immunohistochemistry that primarily makes use of fluorophores to visualize the location of the antibodies on the cells being analyzed.

The term "flow-cytometry" as used herein refers to a laser- or impedance-based, biophysical technology employed in biomarker detection, cell counting, cell sorting, and protein engineering, by suspending cells in a stream of fluid and passing them through an electronic detection apparatus. A flow cytometer allows simultaneous multiparametric analysis of the physical and chemical characteristics of up to thousands of particles per second. Cells are immunostained in solution, and then analyzed by flow cytometry.

The term "antibody" as used herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The antibody can be monoclonal or polyclonal. Monoclonal antibodies have monovalent affinity, in that they bind to the same epitope of the antigen, wherein the epitope is the part of an antigen that is recognized by the antibody. Monoclonal antibodies are derived from identical immune cells that are all clones of a unique parent cell. In contrast, polyclonal antibodies bind to multiple epitopes of the same antigen and are usually made by different B cell lineages.

The term "antigen-binding portion" of an antibody (or simply "antibody portion"), as used herein, refers to one or more fragments of an antibody that retain the ability to specifically bind to an antigen (e.g., TNFα, IL-12). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al, (1989) Nature 341:544-546), which consists of a VH or VL domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. In one embodiment of the invention, the antibody fragment is selected from the group consisting of a Fab, an Fd, an Fd', a single chain Fv (scFv), an scFva, and a domain antibody (dAb).

The terms "level of cells", as well as "reference value", were defined in section 1-A. The different ways to determine the "level of cells with RAD51 foci" were also determined in section 1A.

Regarding the determination of the level of cells with RAD51 foci with respect to the number of cells in the sample that are proliferating, in a preferred embodiment, the number of cells in the sample that are proliferating is determined by determining the expression of a protein selected from the list consisting of Geminin, KI-67, Proliferating cell nuclear antigen, Cyclin A2. In another preferred embodiment, the determination of the expression of the selected protein is carried out by an immunoassay with an antibody specific for the selected protein. Preferably, the cells considered to be proliferating show nuclear expression of the selected protein, wherein "nuclear expression" refers to the expression of the protein localized in the nucleus of the cell. In a preferred embodiment, the cell is defined as having nuclear expression of a protein when the expression of the protein in the nucleus is higher than in the cytoplasm. In a more preferred embodiment, the protein selected is Geminin.

Regarding the determination of the level of cells with RAD51 foci with respect to the number of cells in the sample that show DNA damage, preferably double strand breaks, in a preferred embodiment, the number of cells in the sample that show double strand breaks, is determined by determining the nuclear expression, preferably the presence of nuclear foci, of a protein selected from the list consisting of γH2AX, replication protein A (pRPA), p53 Binding protein 1 (53BP1), double-strand break repair protein (MRE11). In another preferred embodiment, the cell is defined as having nuclear expression of a protein when the expression of the protein in the nucleus is higher than in the cytoplasm. In another preferred embodiment, the cells is defined as having nuclear foci of the selected protein if it contains at least 1, at least 2, at least 3, at least 4, at least 5, at least 6, at least 7, at least 8, at least 9, at least 10, at least 12, at least 15 at least 20 foci of said protein in the nucleus. In a more preferred embodiment, the cell is defined as having nuclear foci of the selected protein if it contains at least 1 focus of said protein in the nucleus. The determination of the presence of nuclear expression, or nuclear foci, of the selected protein is carried out by an immunoassay with an antibody specific for the selected protein, which is preferably γH2AX. In a preferred embodiment, the determination of the number of cells in the sample that show DNA damage, preferably double strand breads, is determined by determining the number of cells with γH2AX nuclear foci, wherein a cell is defined as having nuclear foci of γH2AX if it contains at least 1, at least 2, at least 3, at least 4, at least 5, at least 6, at least 7, at least 8, at least 9, at least 10, at least 12, at least 15 at least 20 foci of γH2AX in the nucleus.

The terms "immunoassay" and methods to detect the protein at a single level were already defined above, as well as the term "antibody" as used herein.

In a preferred embodiment, the sample of any of the methods described so far was isolated from blood, saliva, cerebrospinal fluid, urine, stool, bone marrow, a nipple aspirate, or a solid tumor biopsy. In a yet more preferred embodiment the sample of the methods described so far was isolated from a solid tumor biopsy.

In another particular embodiment, the sample of any of the methods described so far is provided as a fixed tissue, paraffin embedded tissue, formalin-fixed paraffin embedded tissue (FFPE), histological slide, cell suspension, cell pellet, cell slide and/or frozen solid tumor biopsy. In a preferred embodiment the sample is a fixed tissue, wherein fixation was carried with formalin, aldehydes, alcohols, oxidizing agents, mercurial, picrates or with HEPES-Glutamic Acid Buffer Mediated Organic Solvent Protection Effect (HOPE®).

In another embodiment, the response of the subject referred in the method "for predicting the response of a subject diagnosed with cancer to an anti-cancer treatment" can be determined by at least one criteria selected from the group consisting of clinical benefit rate, overall survival, progression free survival, disease free survival, pathologic complete response, clinical complete remission, clinical partial remission, clinical stable disease, recurrence, survival without metastasis, decrease in circulating tumor cells, response of circulating markers and RECIST criteria for tumor response assessment. These different criteria were defined in section 1-A.

The anti-cancer treatment referred in the method "for predicting the response of a subject diagnosed with cancer to an anti-cancer treatment" and/or in the method "for selecting a customized therapy for a subject diagnosed with cancer", preferably comprises the use of surgery. In another embodiment, the anti-cancer treatment referred in any of the above methods of the invention comprises at least one method that induces DNA damage and/or an agent or a combination of agents that target the DNA damage response of the cancer cells. The expression "method that induces DNA damage" was defined in section 1A. Non-limiting examples of methods that induce DNA damage are ionizing radiation, UV light, or chemotherapy with agents directly inducing DNA damage such as those listed in section 1A as "agents directly inducing DNA damage". The expression "agents that target the DNA damage response" as used herein refer to agents that target at least one protein involved in said process in the cell. Non-limiting examples of said proteins are ATM/ATR, BRCA 1/2, BP53, P53, CDC25, CHK1/2, NBS, MRE1J, RAD51, PALB2, PARP or a combination thereof. Non-limiting examples of agents that target the DNA damage response are listed above in section 1-A as "agents that target a protein involved in the DNA damage response of the cell". Preferably, the agent that targets the anti-cancer treatment is selected from the group of PARP inhibitors (including but not limited to olaparib, veliparib, talazoparib, rucaparib, niraparib, CEP-8983, E7016 and BGB-290). The term "PARPi" or "PARP inhibitors" as used herein refers to a group of pharmacological inhibitors of the enzyme poly ADP ribose polymerase (PARP). They are developed for multiple indications, especially for the treatment of cancer. PARP1 is a protein that is important for repairing single-strand breaks in the DNA. If such SSBs persist unrepaired until DNA is replicated (which must precede cell division), then the replication itself can cause DSBs to form. Thus, in general terms, the mechanism of action of drugs that inhibit PARP1 is to cause multiple DSBs formation, so that in tumors with mutations in proteins involved in DSB repair, such as BRCA1, BRCA2 or PALB2, these double strand breaks cannot be efficiently repaired, leading to the death of the cells. Non-limiting examples of PARPi are, as indicated in section 1A, olaparib, veliparib, talazoparib, rucaparib, niraparib, CEP-8983, E7016 and BGB-290.

In another preferred embodiment, the sample referred in any of the previous methods comprises tumor cells characterized by a loss of function of at least one protein involved in the DNA damage response of the cell with DNA damage response deficiencies. The expression "tumor cells characterized by a loss of function of at least one protein involved in the DNA damage response of the cell" was defined in section 1-A. Preferably, the at least one protein involved in the DNA damage response is selected from the group consisting of BRCA1, BRCA2 and/or PALB2. Even more preferably, said at least one protein is BRCA1 and/or BRCA2.

In a particular embodiment, the cancer diagnosed to the subject is selected from the list consisting of breast cancer, ovarian cancer, pancreatic cancer, prostate cancer, lung cancer, colorectal cancer, stomach/gastric cancer, endometrial/uterine/cervical cancer, bladder cancer, head and neck cancer, leukemia, sarcoma, cholangiocarcinoma, glioblastoma, multiple myeloma, lymphoma. More preferable, the cancer diagnosed to the patient is selected from the list consisting of breast cancer, ovarian cancer, and prostate cancer, even preferably it is a breast cancer or an ovarian cancer, yet more preferably it is a breast cancer.

Regarding the treatment received by the subject before the isolation of the sample in any of the aspects of the invention, preferably the subject has not received at any time, preferably within the last 168 hours, more preferably within the last 72 hours, more preferably within the last 48 hours, even more preferably within the last 36 hours, yet more preferably within the last 24 hours, even yet more preferably at 24 hours prior to the isolation of the sample, a chemotherapy selected from the group consisting of AC, FEC, ECF and navelbine/epirubicin. In another preferred embodiment, the subject has not received a chemotherapy selected from the group consisting of AC, FEC, ECF and navelbine/epirubicin at 24 hours prior to the isolation of the sample, but within the last 23 hours, preferably the last 22 hours, more preferably within the last 21 hours, yet more preferably within the last 20 hours, even more preferably within the last 15 hours, even yet more preferably within the last 10 hours, even more preferably within the last 5 hours, and even yet more preferably within the last 2 hours, yet even more preferably within the last hour prior to the isolation of the sample.

In a preferred embodiment, the subject from whom the sample has been isolated has not received any chemotherapy at any time, preferably within the last 168 hours, preferably within the last 72 hours, more preferably within the last 48 hours, even more preferably within the last 36 hours, yet more preferably within the last 24 hours, even yet more preferably at 24 hours prior to the isolation of the sample. In another preferred embodiment, the subject has not received any chemotherapy at 24 hours prior to the isolation of the sample, but within the last 23 hours, preferably the last 22 hours, more preferably within the last 21 hours, yet more preferably within the last 20 hours, even more preferably within the last 15 hours, even yet more preferably within the last 10 hours, even more preferably within the last 5 hours, and even yet more preferably within the last 2 hours, yet even more preferably within the last hour prior to the isolation of the sample.

In a more preferred embodiment, the subject has not received any anti-cancer treatment at any time, preferably within the last 168 hours, more preferably within the last 72 hours, yet more preferably within the last 48 hours, even more preferably within the last 36 hours, yet even more preferably within the 24 hours, even yet more preferably at 24 hours prior to the isolation of the sample. In yet a more preferred embodiment, the subject has not received any anti-cancer treatment at any time before the isolation of the sample.

In another particular embodiment, the subject from whom the sample is isolated has received an anti-cancer treatment at any time in a period prior to the isolation of the sample, preferably within the last 168 hours, more preferably within the last 72 hours, even more preferably within the last 48 hours, even more preferably within the last 36 hours, yet more preferably within the last 24 hours prior to the isolation of the sample. If administered at 24 hours prior to the isolation of the sample, preferably within the last 24 hours prior to the isolation of the sample, said anti-cancer treatment is different from a chemotherapy selected from the group consisting of AC, FEC, ECF and navelbine/epirubicin. In another embodiment, if administered within the last 36 hours, more preferably within the last 48 hours, even more preferably within the last 72 hours, yet more preferably within the last 168 hours, even more preferably at any time prior to the isolation of the sample, said anti-cancer treatment is different from a chemotherapy selected from the group consisting of AC, FEC, ECF and navelbine/epirubicin. Preferably, the treatment of any of the situations described in the present paragraph is the anti-cancer treatment the response to which is being determined in the method "for predicting the response of a subject diagnosed with cancer to an anti-cancer treatment".

In a particular embodiment, the invention relates to a method for determining the maintenance or cease of an anti-cancer treatment in a subject diagnosed with cancer being treated with an anti-cancer treatment, comprising:
  i) determining the level of cells with RAD51 foci in a sample containing tumor cells isolated from said subject wherein the subject has not received, at 24 hours prior to the isolation of the sample, a chemotherapy selected from the group consisting of AC chemotherapy, FEC chemotherapy, ECF chemotherapy and navelbine/epirubicin, and wherein the sample has not been treated with a method that induces DNA damage before determining the level of cells with RAD51 foci, and
  ii) comparing the level obtained in step i) with a reference value, wherein:
    a level of cells with RAD51 foci lower than said reference value then the anti-cancer treatment should be maintained, or
    a level of cells with RAD51 foci equal or higher than said reference value, indicates that the anti-cancer treatment should be ceased.

The terms used in the present method of the invention have been explained in respect to the previous methods of the invention and are equally applicable to the present method.

2. Therapeutic Uses of the Invention

In a fifth aspect, the invention relates to a medicament for use in the treatment of a cancer in a subject, wherein the subject has been identified as responder to said medicament by the method for predicting the response of a subject diagnosed with cancer to an anti-cancer treatment according to the present invention.

In a sixth aspect, the invention relates to a medicament for use in the treatment of a cancer in a subject, wherein the treatment has been designed by a method for selecting a customized therapy for a subject diagnosed with cancer according to the present invention.

The term "medicament" as used herein refers to a composition comprising a therapeutically effective amount of an agent, preferably an anti-cancer agent, more preferably a DNA damaging agent. The medicament also comprises at least one pharmaceutically acceptable excipient or carrier.

In a preferred embodiment, the medicament comprises more than one agent wherein each agent is at its corresponding therapeutically effective amount, preferably at least one of these agents is an anti-cancer agent, and more preferably at least one of these agents is a DNA damaging agent. In another preferred embodiment, the medicament consists on the agent at its corresponding therapeutically effective amount, preferably the anti-cancer agent at its corresponding therapeutically effective amount, more preferably the DNA damaging agent at its corresponding therapeutically effective amount. In this case, the agent already comprises at least one pharmaceutically acceptable excipient or carrier.

The term "therapeutically effective amount", as used herein, refers to the sufficient amount of the agent to provide the desired effect and will generally be determined by, among other causes, the characteristics of the compound itself and the therapeutic effect to be achieved. It will also depend on the subject to be treated, the severity of the cancer disease suffered by said subject, the chosen dosage form, administration route, etc.

Even though individual needs vary, determination of optimal ranges for therapeutically effective amounts of the compounds for use according to the invention belongs to the common experience of those experts in the art. In general, the dosage needed to provide an effective treatment, which can be adjusted by one expert in the art, will vary depending on age, health, fitness, sex, diet, weight, degree of alteration of the molecular pathway being targeted, frequency of treatment, nature and condition of the cancer disease, nature and extent of the cancer, medical condition of the subject, route of administration, pharmacological considerations such as activity, efficacy, pharmacokinetic and toxicology profile of the particular agent used, if using a system drug delivery, and if the agent is administered as part of a combination of drugs.

The expression "pharmaceutically acceptable excipient" or "pharmaceutically acceptable carrier" as used herein refers to any compound or combination of compounds that is essentially non-toxic to the subject at the dosage and concentration employed, and is compatible with the other components of a medicament. Thus, an excipient is an inactive substance formulated alongside the active ingredient (i.e., the agent, preferably the anti-cancer agent, even more preferably the DNA damaging agent such as a PARPi) of a medicament for the purpose of bulking-up compositions that contain said active ingredients. Bulking up allows convenient and accurate dispensation of an active ingredient when producing a dosage form. Excipients also can serve various therapeutic enhancing purposes, such as facilitating the active ingredient absorption or solubility, or other pharmacokinetic considerations. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients depends upon the route of administration and the dosage form, as well as the active ingredient and other factors. An excipient can be a non-toxic solid, semisolid or liquid filler, diluent, encapsulating material or formulation auxiliary of any conventional type. Illustrative, non-limitative, examples of excipients or carriers include water, salt (saline) solutions, alcohol, dextrose, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and the like.

Preferred Embodiments of the Therapeutic Uses of the Invention

In a preferred embodiment, the medicament comprises an anti-cancer agent, more preferably a DNA damaging agent.

In a more preferred embodiment, the medicament comprises a PARP inhibitor agent, preferably selected from the list consisting of olaparib, veliparib, talazoparib, rucaparib, niraparib, CEP-8983, E7016 and BGB-290. In a yet more preferred embodiment, the PARPi is olaparib, veliparib or niraparib, preferably olaparib.

In another particular embodiment, the medicament is for use in a treatment consisting in immunotherapy.

In particular embodiment, the medicament is for use in a treatment, wherein the treatment, in addition to the administration of the medicament, comprises immunotherapy, chemotherapy, radiotherapy or a combination thereof and wherein the subject has been identified responder to said medicament by a method "for predicting the response of a subject diagnosed with cancer to an anti-cancer treatment."

In another particular embodiment, the medicament is for use in a treatment, wherein the treatment, in addition to the administration of the medicament, comprises immunotherapy, chemotherapy, radiotherapy or a combination thereof and wherein the treatment has been designed by a method "for selecting a customized therapy for a subject diagnosed with cancer."

Terms used in context of the medicaments of the invention have the same meaning defined for the methods of the invention.

3. Use of a Kit

In a seventh aspect, the invention relates to the use of a kit in the method "for predicting the response of a subject diagnosed with cancer to an anti-cancer treatment", wherein the kit comprises an antibody that is capable of specifically recognizing the RAD51 protein.

In an eighth aspect, the invention relates to the use of a kit in the method "for selecting a therapy for a subject diagnosed with cancer", wherein the kit comprises an antibody that is capable of specifically recognizing the RAD51 protein.

In a ninth aspect, the invention relates to the use of a kit in the method "for classifying a subject with cancer into a patient cohort", wherein the kit comprises an antibody that is capable of specifically recognizing the RAD51 protein.

In a tenth aspect, the invention relates to the use of a kit in the method "for predicting whether a tumor from a subject is capable of DNA repair by homologous recombination", wherein the kit comprises an antibody that is capable of specifically recognizing the RAD51 protein.

In an eleventh aspect, the invention relates to the use of a kit in any of the methods of the invention, wherein the kit comprises an antibody that is capable of specifically recognizing the RAD51 protein.

In the context of the present invention, "kit" is understood as a product containing the different reagents necessary for carrying out the different uses of the invention packed so as to allow their transport and storage. Additionally, the kits used in the invention can contain instructions for the simultaneous, sequential or separate use of the different components which are in the kit. Said instructions can be in the form of printed material or in the form of an electronic support capable of storing instructions susceptible of being read or understood, such as, for example, electronic storage media (e.g. magnetic disks, tapes), or optical media (e.g. CD-ROM, DVD), or audio materials. Additionally or alternatively, the media can contain internet addresses that provide said instruction.

In a preferred embodiment, the kit referred in any of the uses above, further comprises an antibody capable of specifically recognizing a protein whose expression determines whether a cell in a sample is proliferating. Preferably, said antibody is capable of specifically recognizing a protein selected from the list consisting of Geminin, KI-67, Proliferating cell nuclear antigen, Cyclin A2. More preferably, the protein is Geminin.

In another preferred embodiment, the kit referred in any of the uses above, further comprises an antibody capable of specifically recognizing the presence of a specific protein in the nucleus, preferably the presence of nuclear foci of said protein, wherein said presence in a cell indicates that the cell comprises DNA damage, preferably double strand DNA breaks. Preferably, said antibody is capable of specifically recognizing a protein selected from the list consisting of γH2AX, replication protein A (pRPA), p53 Binding protein 1 (53BP1), double-strand break repair protein (MRE11). More preferably, the antibody is capable of specifically recognizing the γH2AX protein.

In a preferred embodiment, the kit referred in any of the uses indicated in the first, second, third and fourth paragraphs of this section 3, further comprises an antibody selected from the group consisting of an antibody capable of specifically recognizing the Geminin protein, and an antibody capable of specifically recognizing the γH2AX protein or a combination thereof.

In another preferred embodiment, any of the antibodies referred in this section 3 comprise each one at least 10%, at least 20%, at least 30%, at least 40%, at least 50%, at least 60%, at least 70%, at least 80%, at least 90% or at least 100% of the total amount of reagents forming the kits used in the invention.

Terms used in context of the uses of the invention have the same meaning defined for the methods and medicaments of the invention.

The following examples and drawings are provided by way of illustration, and are not intended to be limiting of the present invention.

EXAMPLES

Materials and Methods

Study Design

In order to identify new biomarkers of PARPi efficacy, we prospectively collected tumor samples from patients diagnosed with breast carcinoma (BC) or high-grade serous ovarian cancer (HGSOC) and generated a collection of PDX models. Their sensitivity to PARPi was evaluated, and the functionality of the HRR pathway was analyzed and compared between the PARPi-sensitive vs. the PARPi-resistant PDX samples to find a functional test correlating with response. The functional test was also explored in an independent PDX collection. An exploratory analysis in clinical samples, including patients with germline mutations in BRCA1, BRCA2 or PALB2, was employed to explore the potential clinical interest of the functional test.

Patient-Derived Xenograft (PDX) Models

Fresh tumor samples from patients with breast or high-grade serous ovarian cancer were prospectively collected for implantation into nude mice under protocols approved by Vall Hebron's institutional review board (IRB), Institut Curie or Institut Paoli-Calmettes. Experiments were conducted following the European Union's animal care directive (2010/63/EU) and were approved by the Ethical Committee of Animal Experimentation of the Vall d'Hebron Research Institute (Barcelona, Spain) or by the Ethical Committee of Animal Experimentation CEEA-51 (Evry, France). Fresh primary or metastatic human tumors were obtained from patients at time of surgery or biopsy and immediately implanted into the mammary fat pad (surgery samples) or the lower flank (metastatic samples) of 6-week-old female athymic HsdCpb:NMRI-Foxn1nu mice (Harlan Laboratories). Animals were continuously supplemented with 1 µM 17b-estradiol (Sigma-Aldrich) in their drinking water. Upon growth of the engrafted tumors, the model was perpetuated by serial transplantation onto the lower flank. In each passage, flash-frozen and formalin-fixed paraffin embedded (FFPE) samples were taken for genotyping and histological studies.

Analysis of the BRCA1/2 and PALB2 Genes

DNA was extracted from PDX tumor samples or patient peripheral blood and next generation sequencing of the BRCA1, BRCA2 and PALB2 genes was performed.

In Vivo Experiments of PDX Sensitivity to PARPi

To evaluate the sensitivity to PARP inhibition, tumor-bearing mice were equally distributed into treatment groups of 5 to 10 mice with tumors ranging 70 to 300 mm3. Olaparib 50 mg/kg or 100 mg/kg, Niraparib 75 mg/kg or 50 mg/kg, or Veliparib 100 mg/kg were administered per gavage (p.o.) daily (in 10% v/v DMSO/10% w/v Kleptose [HP-β-CD]). Tumor growth was measured with caliper bi-weekly from first day of treatment to day 21 and every 7-10 days in the acquired resistance setting. To generate PDX models with acquired resistance to PARPi, olaparib treatment was maintained for up to 150 days in olaparib-sensitive tumors until individual tumors regrew. In all experiments, mouse weight was recorded twice weekly. The tumor volume was calculated as V=4π/3/Lx12, "L" being the largest diameter and "1" the smallest. Mice were euthanized when tumors reached 1500 mm3 or in case of severe weight loss, in accordance with institutional guidelines. The antitumor activity was determined by comparing tumor volume at 21 days to its baseline: % tumor volume change= (V21 days−Vinitial)/Vinitialx100. For olaparib-sensitive PDX, the best response was defined as the minimum value of % tumor volume change sustained for at least 10 days. To classify the antitumor response, the Response Evaluation Criteria In Solid Tumors (RECIST) criteria on the % tumor volume change was followed: CR (complete response), best response<−95%; PR (partial response), −95<best response<−30%; SD (stable disease), −30%<best response<+20%, PD (progressive disease), best response>+20%.

Immunofluorescence

The following primary antibodies were used for immunofluorescence: rabbit anti-RAD51 (Santa Cruz Biotechnology H-92, dilution 1:250), rabbit anti-RAD51 Ab from Cell Signalling Technologies (CST #8875, dilution 1:25 from a 83 µg/ml stock), rabbit anti-RAD51 Ab from Abcam (ab-133534, dilution 1:1000), mouse anti-Geminin (NovoCastra NCL-L, 1:100 in PDX samples, 1:60 in patient samples), rabbit anti-Geminin (ProteinTech 10802-1-AP, 1:400), mouse anti-BRCA1 (Santa Cruz Biotechnology D-9, 1:50 for C-term; or Abcam MS110, 1:200 for N-term), and mouse anti-γH2AX (Millipore JBW301, 1:200). The secondary antibodies used were: goat anti-rabbit Alexa fluor 568 (Invitrogen; 1:500), goat anti-mouse Alexa fluor 488 (Invitrogen; 1:500), goat anti-mouse Alexa fluor 568 (Invitrogen; 1:500) and goat anti-rabbit Alexa fluor 488 (Invitrogen; 1:500).

Thin tissue sections were deparaffinized with xylene and hydrated with decreasing concentrations of ethanol. For target antigen retrieval, sections were microwaved for 4 minutes at 110° C. in DAKO Antigen Retrieval Buffer pH 9.0. Sections were cooled down in distilled water for 5 minutes, then permeabilized with DAKO Wash Buffer (contains Tween 20) for 5 minutes, followed by incubation in blocking buffer (DAKO Wash Buffer with 1% bovine serum albumin) for 5 minutes. Primary antibodies were diluted in DAKO Antibody Diluent and incubated at room temperature for 1 hour. Sections were washed for 5 minutes in DAKO Wash Buffer followed by 5 minutes in blocking buffer. Secondary antibodies were diluted in blocking buffer and incubated for 30 minutes at room temperature. The 2-step washing was repeated followed by 5 minutes incubation in distilled water. Dehydration was performed with increasing concentrations of ethanol. Sections were mounted with DAPI ProLong Gold antifading reagent and stored at −20° C. Immunofluorescence images were acquired at 600× magnification using Olympus DP72 microscope and generated images using CellSens Entry software.

RAD51 was quantified by scoring: a) the percentage of tumor cells with RAD51 nuclear foci, b) the percentage of γH2AX foci positive cells with RAD51 foci, or c) the percentage of geminin positive cells with RAD51 foci, as indicated in the Figures. Scoring was performed blindly onto life images. Optimally, one-hundred geminin or γH2AX foci-positive cells from at least 3 different and representative areas of each sample were analyzed. When available, 3 biological replicates of each PDX model (both vehicle- and olaparib-treated) were studied.

Immunohistochemistry

IHC staining of RAD51 and Geminin on patient-derived tumor xenograft (PDX) tissue was also developed on the Ventana Ultra Discovery platform. Thin sections of FFPE tissues were deparaffinized using EZ Prep (Ventana) and then antigen retrieved using Cell Conditioning 1 (CC1) solution (Ventana) at 98° C. for 32 minutes. Slides were blocked for 32 minutes at 36° C. using blocking reagent of Mouse on Mouse (M.O.M) Blocking Reagent (Vector Laboratories) diluted in SignalStain Antibody Diluent (Cell Signaling Technology), and then blocked for 4 minutes with Discovery Inhibitor (Roche). Slides were incubated for 32 minutes at 36° C. with a cocktail of anti-RAD51 (CST #8875 at 6.6 µg/ml) and anti-Geminin (Leica Geminin-NCL-L, dilution 1:10) antibodies in Ventana Antibody Diluent with Caesin (Roche). Detection was carried out using UltraMap anti-Rb HRP for 16 minutes (Roche), UltraMap anti-Ms AP (Roche) for 12 minutes, and then the Purple and Yellow kits (Roche) each for 32 minutes. Nuclei were counter stained with Haematoxylin for 4 minutes. Slides were then washed in soapy water, rinsed and dried for 30 minutes at 60° C., before being dipped in xylene and coverslipped. Wash steps were automated and performed using 1× Reaction Buffer (Roche). All slides were scanned using a Zeiss Axio Z1 scanner with a 40× objective and a minimum of 4 Z-stacks.

Analysis of RAD51 mRNA Expression

RNA was extracted from PDX samples (15-30 mg) by using the PerfectPure RNA Tissue kit (5 Prime). The purity and integrity was assessed by the Agilent 2100 Bioanalyzer system and cDNA was obtained using the PrimeScript RT Reagent kit (Takara).

Quantitative RT-PCR was performed in a 7900HT Fast Real-Time PCR System (Applied Biosystems) using TaqMan Universal Master Mix II (Applied Biosystems) and predesigned human specific primers and TaqMan probes (Hs99999908_m1 for GUSB, Hs99999903_m1 for ACTB and Hs00153418 ml for RAD51). The comparative CT method was used for data analysis, in which geNorm algorithms were applied to select the most stably expressed housekeeping genes (GUSB and ACTB) and geometric means were calculated to obtain normalized CT values.

Patient Cohort

The cohort consisted of breast and ovarian cancer patients from the Vall d'Hebron University Hospital, with FFPE material representative of the disease and signed IRB-approved informed consent form. Immunofluorescence analysis and RAD51 foci quantification was performed as described for FFPE PDX tumor samples.

Statistical Analysis

All statistical tests were performed with GraphPad Prism version 7.0. Paired or unpaired t test (two-tail) was calculated and p values given. Error bars represent SEM of at least three biological replicates, unless otherwise stated.

Example 1. The Antitumor Activity of Olaparib in PDXs Identifies a Subset of PARPi-Sensitive Tumors that Present HRR-Related Alterations The antitumor activity of the PARPi olaparib was assessed in 39 PDX models of breast cancer (BrC), 3 PDX models of ovarian cancer (HGSOC/OvC) and 2 PDX of pancreatic cancer (PaC) (FIG. 1). For this purpose, fresh tumor samples were collected from BrC, HGSOC or PaC patients, and implanted into nude mice to generate experimental PDX models. Treatment with olaparib exhibited antitumor activity in ten PDX models as assessed by RECIST: complete response (CR, n=6), partial response (PR, n=2), and stable disease (SD, n=2). All these PARPi sensitive PDX carried gBRCA1/2 gene mutations or functional alterations in the homologous recombination repair (HRR) pathway, including mutations in PALB2 or hypermethylation of the BRCA1 promoter. The remaining 34 PDX models, which derived from BRCA mutated and BRCA wild-type patients, were olaparib-resistant (PD, progressive disease). This PDX cohort was used to study clinically relevant mechanisms of PARPi sensitivity and acquired-resistance in vivo.

Figure 2:
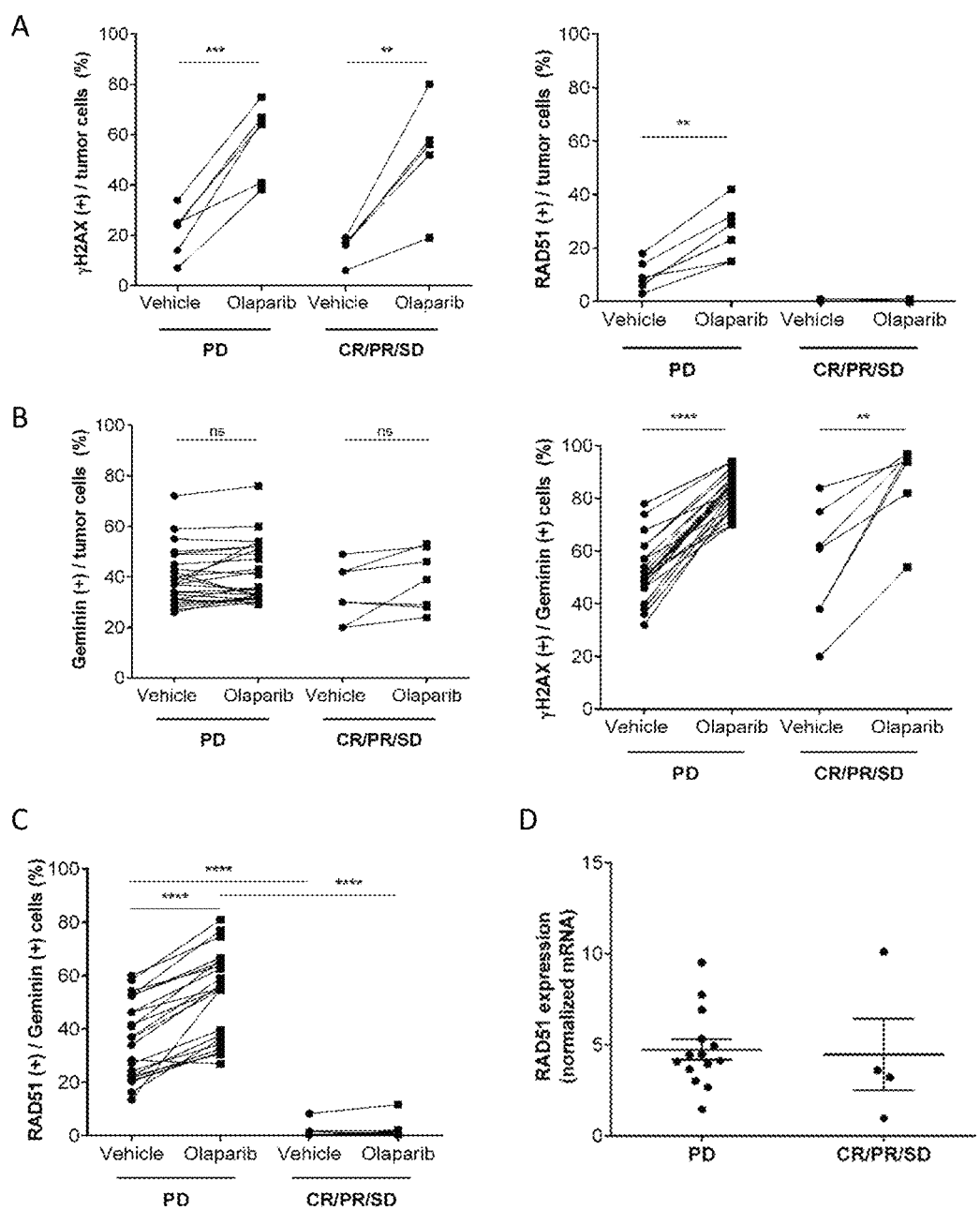
FIG. 2 shows that untreated tumors have detectable levels of cell proliferation, DNA damage and RAD51 foci formation. (A) Percentage of γH2AX and RAD51 nuclear foci containing tumor cells detected by immunofluorescence in a small subset of formalin-fixed paraffin embedded (FFPE) samples from untreated (Vehicle) and treated (Olaparib) PDX tumors shown in FIG. 1. We quantified γH2AX foci as a marker of DNA damage by DSB, and RAD51 foci as a marker of functional HRR. Tumors are classified according to their olaparib response, i.e. resistant (PD) vs sensitive (CR/PR/SD) tumors, as a similar endpoint to the Clinical Benefit Rate used in the clinic. As expected, olaparib induces γH2AX foci formation in both groups. RAD51 foci formation is only significantly induced in the olaparib resistant PDX models. Importantly, baseline levels of γH2AX and RAD51 foci are detected in vehicle-treated tumors supporting the idea that functional HRR proteins can be assessed in untreated samples. (B) Quantification of geminin-positive cells as a marker of S/G2-cell cycle (indicates that tumor cells are in the cell cycle of DNA synthesis) and γH2AX-positive cells in geminin-positive cells in tumors, classified according to their olaparib response. Comparable levels of geminin-positive cells are observed in both groups, ranging from 20 to 70% of the total cells. Olaparib treatment significantly increases γH2AX foci formation in both sensitive and resistant tumors. Neither geminin levels nor γH2AX foci distinguishes PARPi sensitive from PARPi resistant tumors. As in panel A, untreated tumors exhibit marked levels of endogenous DNA damage (γH2AX foci). (C) Quantification of geminin-positive cells with RAD51 nuclear foci, from now on also named as RAD51 score, provides an estimate of the proportion of cells in S/G2-phase of the cell cycle with functional HRR. The percentage of RAD51 foci/geminin-positive cells is significantly increased in olaparib-treated samples from resistant PDX models. Remarkably, the baseline levels of RAD51 foci/geminin-positive cells of resistant tumors is well above the baseline of sensitive tumors. Therefore, subsequent analyses are done in untreated tumors. (D) Levels of RAD51 mRNA expression in untreated PARPi resistant and sensitive PDX tumor samples, measured by quantitative reverse transcription polymerase chain reaction (qRT-PCR). The deficiency in RAD51 foci formation in PARPi sensitive tumors shown in FIGS. 2A and 2C is not due to lack of RAD51 expression. Paired t test: , <0.01; *, <0.001; ****, <0.0001.

Example 2: Untreated Tumors have Detectable Levels of Cell Proliferation, DNA Damage and RAD51 Foci Formation The functional status of HRR was further investigated in formalin-fixed paraffin-embedded (FFPE) tumors from the above PDX cohort. Tumors were classified according to their olaparib response, i.e. resistant (PD) vs sensitive (CR/PR/SD), as a similar endpoint to the Clinical Benefit Rate used in the clinic. Specifically, in a subset of FFPE samples from untreated (vehicle) and treated (olaparib) PDX tumors, the percentage of tumor cells with γH2AX or RAD51 nuclear foci detected by immunofluorescence was scored (FIG. 2A). γH2AX foci was used as a marker of double-strand DNA damage and RAD51 foci as a marker of HRR. As expected, olaparib treatment increased γH2AX foci formation in all tumors. Untreated samples already had detectable baseline DNA damage levels. RAD51 foci were clearly detected in resistant models and increased with olaparib treatment. In olaparib-sensitive tumors, RAD51 foci were very low or undetectable despite γH2AX foci formation.

Then, the percentage of geminin and γH2AX foci positive cells was assessed (FIG. 2B). Geminin was used as a marker of the S/G2-phase of the cell cycle and, thus, of cell proliferation. Comparable levels of cell proliferation were observed in all groups. Olaparib treatment increased γH2AX foci formation in both sensitive and resistant tumors.

The percentage of RAD51 positive cells in geminin positive cells, from now on also called RAD51 score, was then determined in cells of both untreated (vehicle) and treated (olaparib) PDX samples (FIG. 2C). Trends between untreated and treated samples were comparable, thus subsequent studies and analyses were done in the former group, i.e. samples from untreated individuals.

The reduced RAD51 foci formation in sensitive tumors was not the result of decreased RAD51 expression (FIG. 2D) but rather suggested a reduced localization of RAD51 proteins (i.e. RAD51 loading on DNA to repair) and, thus, a dysfunctional HRR pathway.

Altogether, these data show that low percentage of tumor cells with RAD51 nuclear foci identified by the RAD51 assay is associated with PARPi sensitivity, and that high percentage of tumor cells with RAD51 nuclear foci is associated with PARPi resistance in the PDX cohort.

Figure 3:
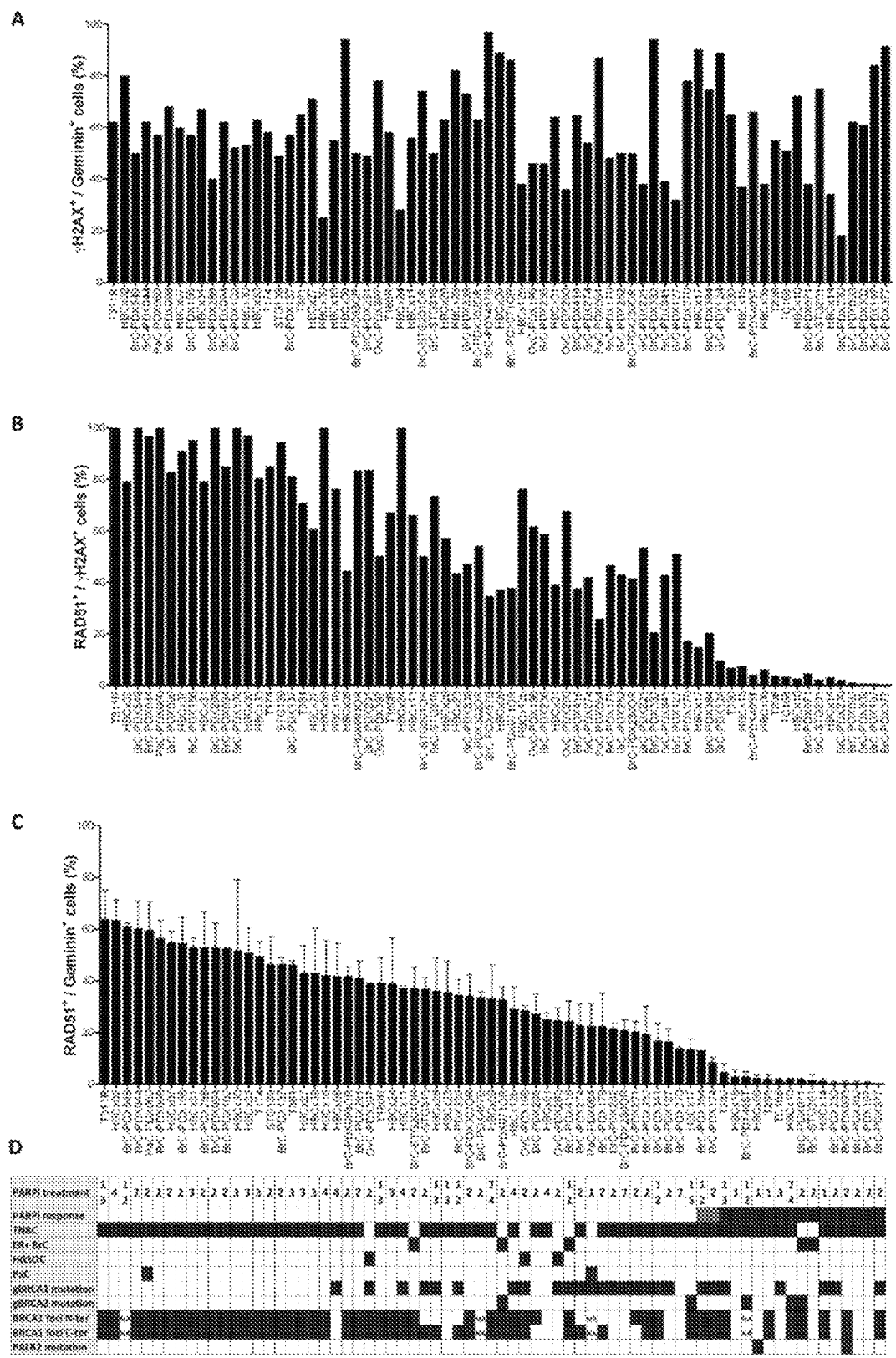
FIG. 3 shows that low RAD51 foci formation is associated with PARPi-sensitivity in a multicenter panel of 71 PDX models. (A) The percentage of γH2AX foci positive cells in geminin-positive cells shows that there is DNA damage in all tumors independently of PARPi response. Quantification of γH2AX foci is necessary to avoid misclassification of low RAD51 tumors due to lack of DNA damage, instead of HRR deficiency. (B) The percentage of RAD51 foci-positive/γH2AX foci-positive cells shows lower levels in sensitive tumors. (C) Quantification of RAD51 foci/geminin-positive cells (RAD51 score), showing that all PARPi sensitive tumors exhibit a low RAD51 score. (D) Table summarizing the different characteristics of each PDX model, including the PARPi treatment and dose (1 for Olaparib 100 mg/kg, 2 for Olaparib 50 mg/kg, 3 for Niraparib 75 mg/kg, 4 for Niraparib 50 mg/kg and 5 for Veliparib 100 mg/kg), the PARPi response (black, CR/PR; grey, SD; and white, PD), the tumor of origin, the presence of mutations in BRCA1 or BRCA2 genes, the presence of BRCA1 foci detected with an anti-BRCA1 antibody against the N-terminal (N-ter) or C-terminal (C-ter) region of BRCA1, and the presence of mutations in PALB2. Filled squares in black indicate positivity for that trait. NA, data not available; TNBC, Triple Negative Breast Cancer; ER+BrC, Estrogen Receptor positive breast tumors; HGSOC or OvC, High-Grade Serous Ovarian Cancer; gBRCA, germline BRCA1/2-mutated.

Example 3: Low RAD51 Nuclear Foci Formation Identifies PARPi-Sensitive PDX Tumors in a Multicenter Panel of 71 PDX Models A multicenter panel with PDX from VHIO (n=44, FIG. 1) and PDX from XenTech (n=27) was used to develop and pre-clinically validate the RAD51 assay. The percentage of γH2AX foci positive cells in Geminin positive cells was assessed (FIG. 3A). Results showed that DNA damage occurs in all tumors independently of PARPi response. However, the percentage of RAD51 foci positive cells in γH2AX foci positive cells or in geminin positive cells correlated with the PARPi response (FIG. 3B-D). Indeed, all tumors from PARPi sensitive PDX, showed a lower percentage of RAD51 foci positive cells within geminin positive cells compared to PARPi resistant PDX. Most samples showing PARPi sensitivity carried mutations in the BRCA1/2 or PALB2 genes (n=12 mutated of 17 sensitive models) and seven did not show BRCA1 foci formation (FIG. 3D). These results support the potential of the RAD51 assay as a predictive biomarker of functional HRR and PARPi response, especially, but not exclusively, in tumors with some type of deficiency in at least one protein involved in the DNA damage response.

Figure 4:
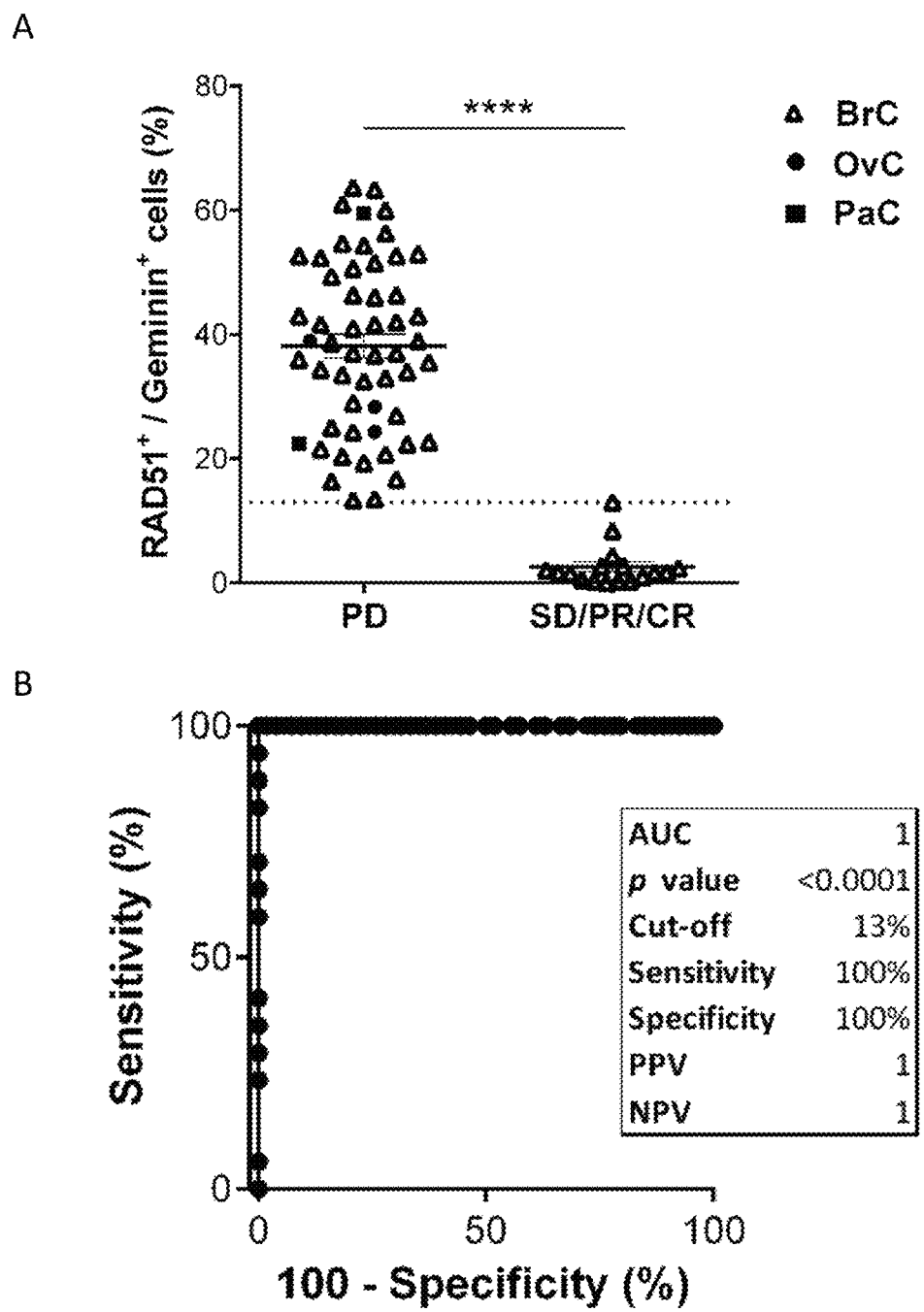
FIG. 4 shows that the RAD51 score accurately discriminates tumors that are resistant and sensitive to PARP inhibitors. (A) Dot plot representing the scores shown in FIG. 3C. PARPi-resistant tumors exhibit a significantly higher level of RAD51 foci/geminin-positive cells than PARPi-sensitive tumors. The dotted line represents the cut-off (13%) that discriminates tumors that are resistant or sensitive to PARPi, based on the likelihood ratio that maximizes sensitivity and specificity in the Receiver-Operating Characteristic (ROC) curve. Of note, the two PDX models (i.e. PDX124 and PDX384) with higher RAD51 foci levels in the sensitive group showed a SD to PARPi. **** $p<0.0001$, t-test. (B) ROC curve depicting the sensitivity vs specificity, and performance measures (insert), of the RAD51 score for predicting PARPi response, based on individual PDX-derived tumor values. PPV, positive predictive value; NPV, negative predictive value.

Example 4: The Evaluation of RAD51 Foci Formation Accurately Associates with PARPi Response To further confirm that the RAD51 score associates with PARPi response, the results from FIG. 3C were analyzed with a Receiver Operating Characteristic (ROC) curve (FIGS. 4A and B). In this PDX cohort, results show that the RAD51 score discriminates with 100% sensitivity and 100% specificity tumors that are sensitive vs resistant to PARPi treatment.

Figure 5:
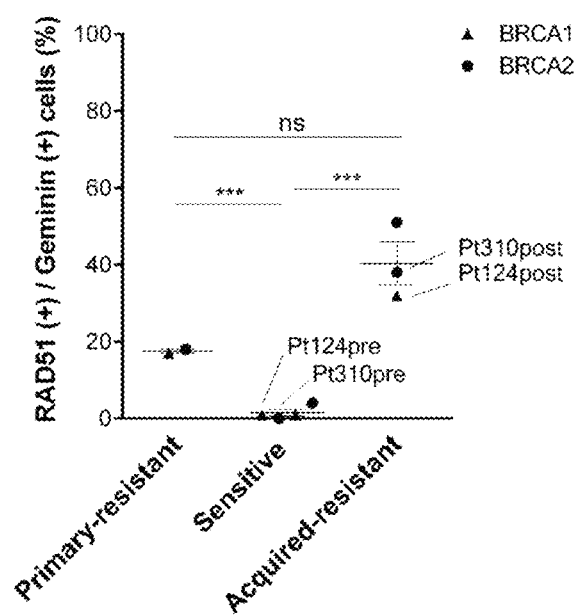
FIG. 5 shows the clinical validation of the RAD51 assay in a breast cancer patient cohort. (A) The level of RAD51 foci formation in geminin-positive cells discriminates patients whose tumors were olaparib sensitive from those that were resistant. Data include samples from two patients (Pt) with primary PARPi-resistance (one sample from a skin metastasis of a gBRCA1 BrC patient, and another sample from a lymph node metastasis of a gBRCA2 BrC patient) and four PARPi-sensitive patients (one sample from a liver metastasis of Pt310pre with gBRCA2 BrC, one sample from a mastectomy of Pt124pre with gBRCA1 BrC, one sample from a lymph node metastasis of a gBRCA1 BrC patient and another sample from a peritoneal implant of a gBRCA1 HGSOC patient). For acquired resistance, data includes samples obtained from three patients at PARPi progression (a sample from a liver metastasis of Pt310post with gBRCA2 BrC, another sample from a skin metastasis of a gBRCA1 BrC patient, and a last sample from a skin metastasis of a gBRCA2 BrC patient). Unpaired t test: ***, <0.001. (B) RAD51 foci/geminin positivity in FFPE tumor samples from patients with hereditary breast or ovarian cancer. The box underneath summarizes different characteristics of each patient and the presence or absence of BRCA1 nuclear foci in the analyzed tumors. Of note, tumors from PALB2-mutated patients and tumors without BRCA1 foci showed low RAD51 scores, supporting the predictive value of RAD51 in identifying functional HRR alterations in clinical samples. FH, Family History; *, Tumors with a pathogenic mutation in PALB2 gene. (C) and (D) Quantification of RAD51 and γH2AX foci formation in "treatment naïve" patient tumor samples, (i.e. in patients that have never received an anti-cancer treatment) and in tumor samples "with prior treatment". Ten "treatment-naïve" primary breast tumors from gBRCA1/2 patients, either from the diagnostic biopsy (n=6) or the surgery tumor (n=4) were scored for RAD51 and γH2AX foci. Ten primary or metastatic breast tumors "with prior treatment" from gBRCA1/2 patients, either from their surgery specimen after having received neoadjuvant therapy—including a DNA damaging agent—(n=3) or from the metastatic setting (n=7), were scored for RAD51 and γH2AX foci. In total, we analyzed 10 BRCA1—plus 10 BRCA2-mutated tumors. This data confirms that RAD51 is evaluable in treatment-naïve tumor samples as well as in samples from patients that have received chemotherapy.
Figure 5:
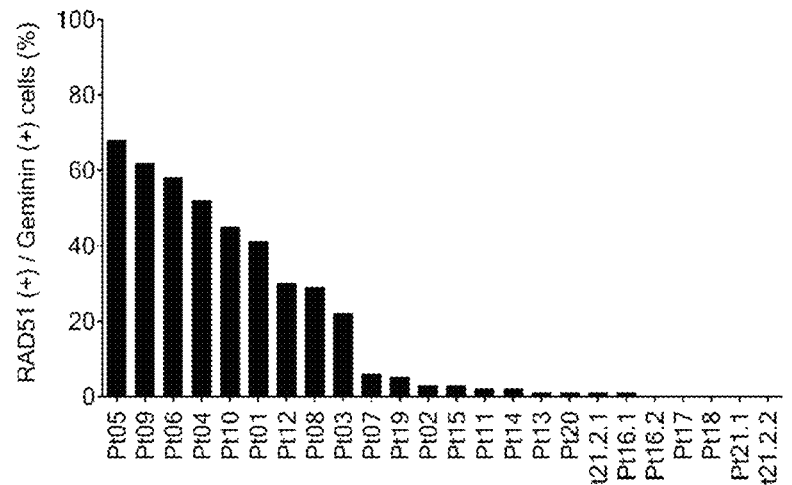
Figure 5:
Figure 5:
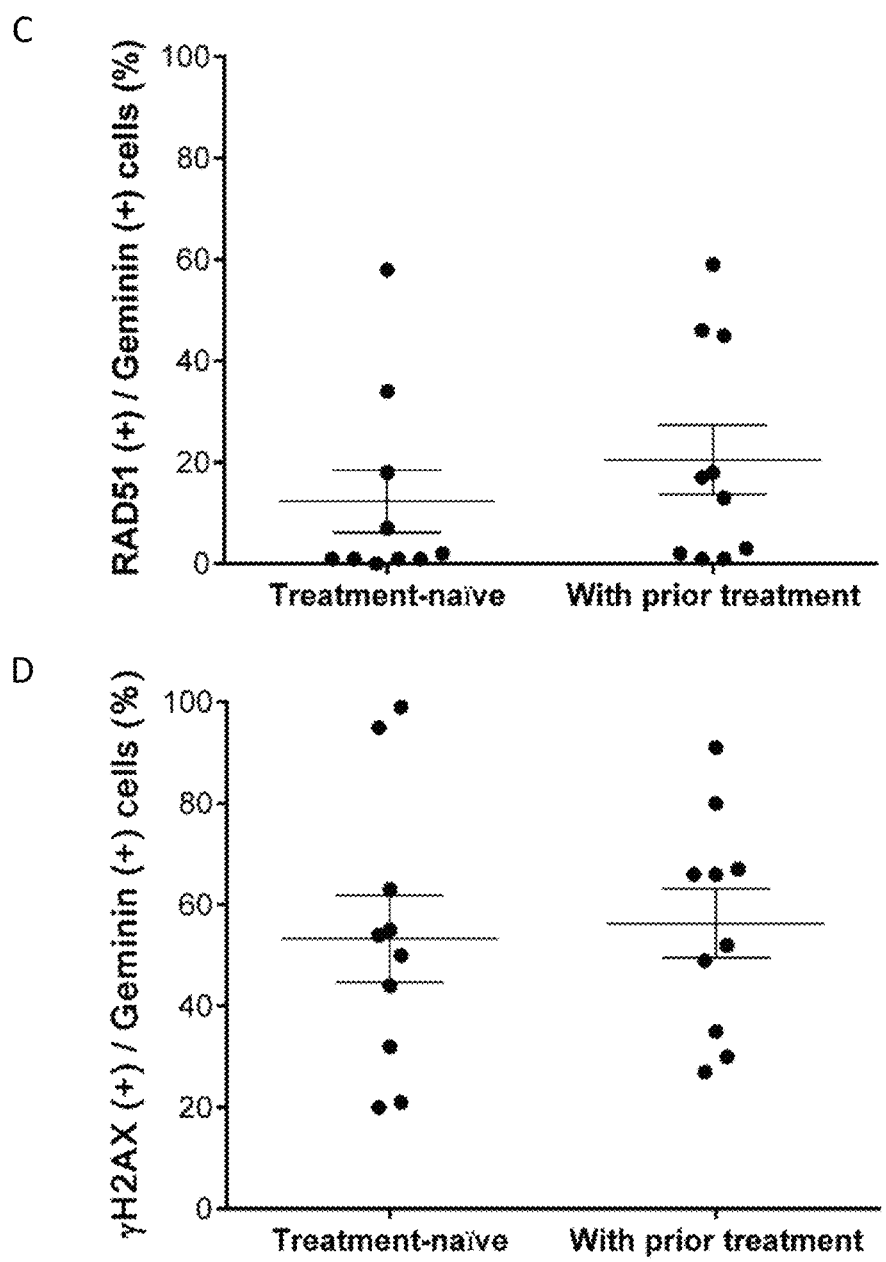

Example 5: The RAD51 Score Predicts PARPi Response in Untreated Clinical Samples Additionally, a clinical validation of the accuracy of the RAD51 score to discriminate patients with PARPi sensitive vs resistant tumors was carried out. Data results from samples, including skin, liver, peritoneal and lymph node metastasis, from gBRCA1 or gBRCA2 BrC or HGSOC patients. Data from two patients with primary PARPi-resistance, four PARPi-sensitive patients, and three patients at PARPi progression are shown (FIG. 5A). These results show that the determination of the percentage of cells with RAD51 nuclear foci accurately associates with PARPi response, and supports its potential use in the clinic.

Next, we extended the clinical validation in 24 samples from a total of 21 patients without gBRCA mutations (FIG.

5B). As it is well known that PALB2 is essential for HRR, we enriched our patient cohort with 12 tumors from patients harboring germline mutations in PALB2 (gPALB2). Fifteen out of 24 tumor samples showed low RAD51 positivity 6%), including all twelve gPALB2 tumor samples. Interestingly, the three tumors with low RAD51 that lacked gPALB2 mutations showed lack of BRCA1 nuclear foci by immunofluorescence, suggesting that BRCA1 promoter hypermethylation might be the cause of HRR-deficiency. Thus, these results confirm that the RAD51 assay identifies HRR-deficient tumors that may benefit from PARPi therapy beyond BRCA-related cancers.

Finally, we measured RAD51 foci (FIG. 5C) and γH2AX foci (FIG. 5D) formation in 20 gBRCA tumor samples (n=10 BRCA1 and n=10 BRCA2 mutated), including 10 treatment-naïve primary breast cancer tumors (i.e. from patients that have never received an anti-cancer treatment) and 10 tumors from patients who received prior treatment in the early/metastatic setting. Of note, endogenous DNA damage was detected in all tumors, including treatment-naïve primary breast cancers. Furthermore, RAD51/geminin positivity ranges 0-58% in treatment naïve samples, a range that is similar to tumors from patients that have received chemotherapy. Thus, this test is highly sensitive and confirms the feasibility to detect RAD51 foci in treatment-naïve samples, suggesting that HRR recovery can be present at diagnosis.

Example 6: The RAD51 Score is Higher in Disease Relapsed than in Non-Relapsed gBRCA-Mutated Breast Cancer Patients We explored the potential predictive value of the RAD51 score to anticipate disease outcome at long-term. To this end, the RAD51 assay was performed in untreated primary tumors from a retrospective cohort of 19 gBRCA-mutated BrC patients. Clinical information of the patients is provided in Table 1.

TABLE 1

Clinical information of the patients analyzed in the present example, summarizing BRCA status, tumor subtype, TNM stage, disease relapse and anti-cancer therapy for this cohort of patients.

| Patient | germline BRCA 1/2 | Tumor subtype | TNM stage | Disease Relapse | Anti-cancer therapy | | |
|---|---|---|---|---|---|---|---|
| | | | | | NeoAdj CTx | Surgery | Adj CTx |
| BrC-001 | 1 | TNBC | T3N1M0 | YES | PTX + CB -> AC | YES | |
| BrC-002 | 1 | TNBC | T4N2M0 | YES | | YES | TC |
| BrC-003 | 2 | lum | T2N1M0 | YES | | YES | AC -> PTX |
| BrC-004 | 1 | TNBC | T2N0M0 | YES | ERI | YES | AC |
| BrC-005 | 2 | lumB | T2N0M0 | YES | AC -> PTX | YES | |
| BrC-006 | 1 | TNBC | T2N1M0 | YES | AC -> DTX | YES | |
| BrC-007 | 2 | TNBC | T2N1M0 | YES | | YES | TAC |
| BrC-008 | 1 | TNBC | T2N0M0 | YES | | YES | EC -> PTX |
| BrC-009 | 1 | TNBC | T2N0M0 | YES | | YES | DTX |
| BrC-010 | 2 | lum | T2N1M0 | YES | | YES | ET -> CPC |
| BrC-011 | 2 | lumB | T2N1M0 | NO | | YES | TAC |
| BrC-012 | 2 | lumB | T1N2M0 | NO | | YES | unk (standard) |
| BrC-013 | 1 | lumB | T3N1M0 | NO | L-DOX + CP -> PTX | YES | |
| BrC-014 | 1 | TNBC | T2N1M0 | NO | | YES | AC -> PTX |
| BrC-015 | 1 | TNBC | T2N1M0 | NO | | YES | unk (standard) |
| BrC-016 | 2 | lumA | T3N2M0 | NO | | YES | AC -> DTX |
| BrC-017 | 2 | lumB | T1N1M0 | NO | | YES | AC -> PTX |
| BrC-018 | 1 | TNBC | T3N1M0 | NO | AC -> PTX | YES | |
| BrC-019 | 1 | lumB | T3N0M0 | NO | | YES | AC -> PTX |

Tumor subtype: lumA, luminal A; lumB, luminal B; lum, luminal (not specified).

Type of treatment: PTX, paclitaxel; CP, cyclophosphamide; AC, doxorubicin + CP; L-DOX, liposomal doxorubicin; CB, carboplatin; DTX, docetaxel; ERI, eribulin; ET, epirubicin + DTX; CPC, capecitabine; TC, DTX + CP; TAC, DTX + doxorubicin + CP; unk, unknown standard chemotherapy due to information not available in clinical records.

due to information not available in clinical records.

Figure 6:
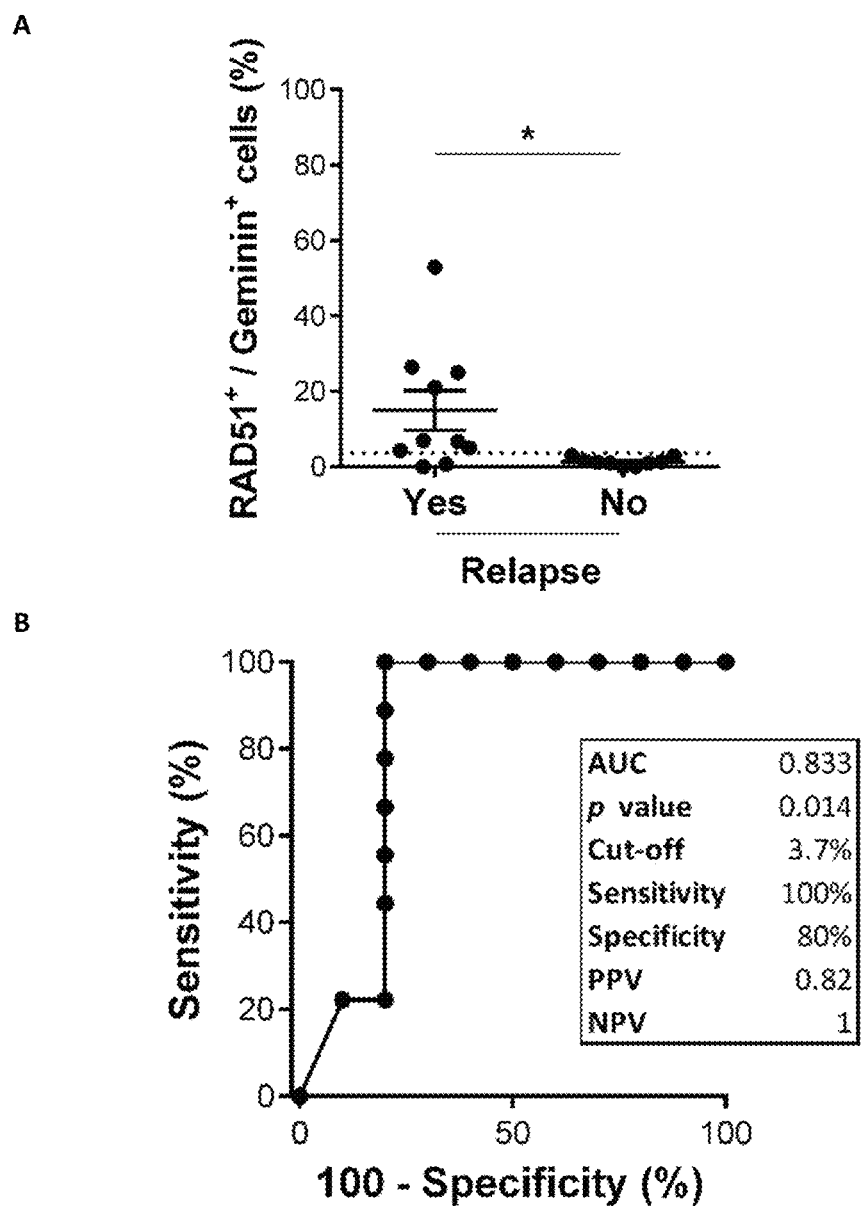
FIG. 6 shows that the RAD51 score is higher in disease relapsed patients than in non-relapsed ones, in a retrospective cohort of gBRCA-mutated breast cancer patients (n=19). All patients received radical surgery of primary tumors and standard chemotherapy (CTx), either in the neoadjuvant (NeoAdj), or adjuvant (Adj) setting. The RAD51 assay was performed in diagnostic biopsies or surgical specimens from treatment-naïve tumors. The relapse and no-relapse groups were balanced for classical prognostic factors. (A) Dot plot showing the RAD51 score in patients stratified by occurrence or not of disease relapse. Tumors from patients with a good disease outcome (i.e. no relapse after >5 years of follow-up) had low RAD51 foci levels, i.e. RAD51 score below 3.7% (dotted line). Patients with a poor disease outcome (i.e. relapsed) showed variable levels, being the patient with an earliest relapse (11 months after diagnosis) the one showing the highest RAD51 score (53% of RAD51 foci/geminin positive cells). The dotted line represents the cut-off that discriminates tumors from patients who relapsed or not, based on the likelihood ratio that maximizes sensitivity and specificity in the Receiver-Operating Characteristic (ROC) curve. *, p=0.026, t-test. (B) ROC curve of sensitivity vs specificity and performance measures (insert) of the RAD51 score for predicting disease outcome. PPV, positive predictive value; NPV, negative predictive value.

All patients received radical surgery of breast tumors and standard chemotherapy, either in the neoadjuvant or adjuvant settings. All patients that did not relapse (after >5 years of follow-up) showed low RAD51 scores. In contrast, the level of RAD51 foci formation was higher in tumors from patients presenting a poor disease outcome, i.e. relapsed (FIG. 6A). The relapse and no-relapse groups were balanced for classical prognostic factors and were discriminated by the RAD51 score with 100% sensitivity and 80% specificity (FIG. 6B). Thus, the RAD51 assay predicts clinical response after standard anti-cancer therapy.

Figure 7:
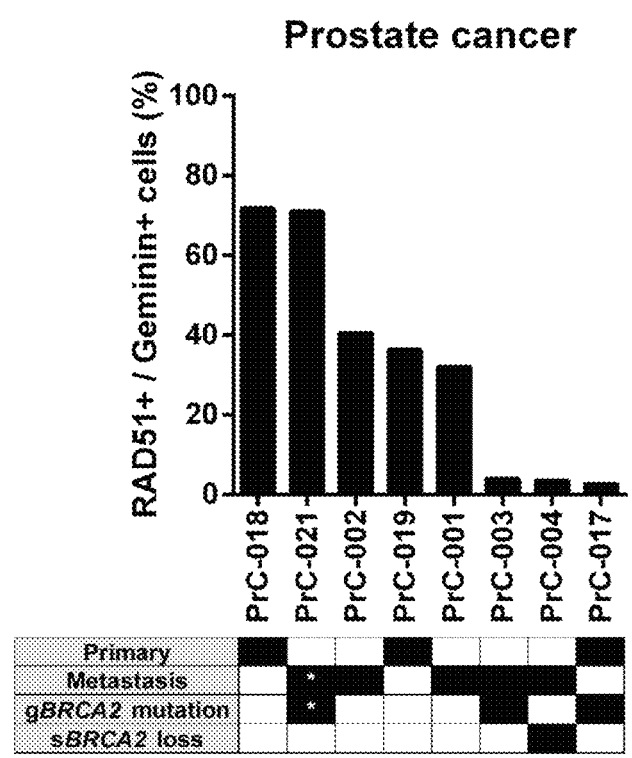
FIG. 7 shows the RAD51 score in samples from prostate cancer patients (n=8). The RAD51 assay was successfully performed in primary prostatectomies (n=3) and metastatic tissues (n=5), including liver, bone marrow and lymph node metastatic biopsies. Three samples (PrC-003, PrC-004 and PrC-017) show low levels of RAD51 foci, in association with genomic alterations in BRCA2 (two germline BRCA2-mutated tumors—gBRCA2- and one somatic BRCA2 loss—sBRCA2-). Of note, sample PrC-021 (*), derived from a gBRCA2 mutated patient, was obtained after developing resistance to carboplatin (seven months post treatment). High RAD51 foci levels in this sample suggests reversion of HRR deficiency that likely resulted from long exposure to this DNA damaging drug. Thus, the RAD51 score stratifies prostate tumors based on HRR proficiency (n=5) and deficiency (n=3) in the clinics.

Example 7: The RAD51 Score Identifies a Subset of Prostate Cancers with HRR Alterations The RAD51 assay was successfully performed in prostate cancers (Pr) and derived metastases (FIG. 7). Low levels of RAD51 foci were detected in three samples carrying a genomic or somatic alteration in BRCA2. Of note, sample PrC-021, derived from a gBRCA2-mutated patient, was obtained after developing resistance to the standard chemotherapy carboplatin. High RAD51 foci levels in this sample suggests reversion of HRR deficiency that likely resulted from long exposure (in particular, seven months) to this DNA damaging drug. Four other BRCA wild-type samples showed a high RAD51 score. Thus, the RAD51 score stratifies prostate tumors based on HRR proficiency and deficiency. This data supports the use of PARPi in patients with prostate cancer with a low RAD51 score.

Figure 8:
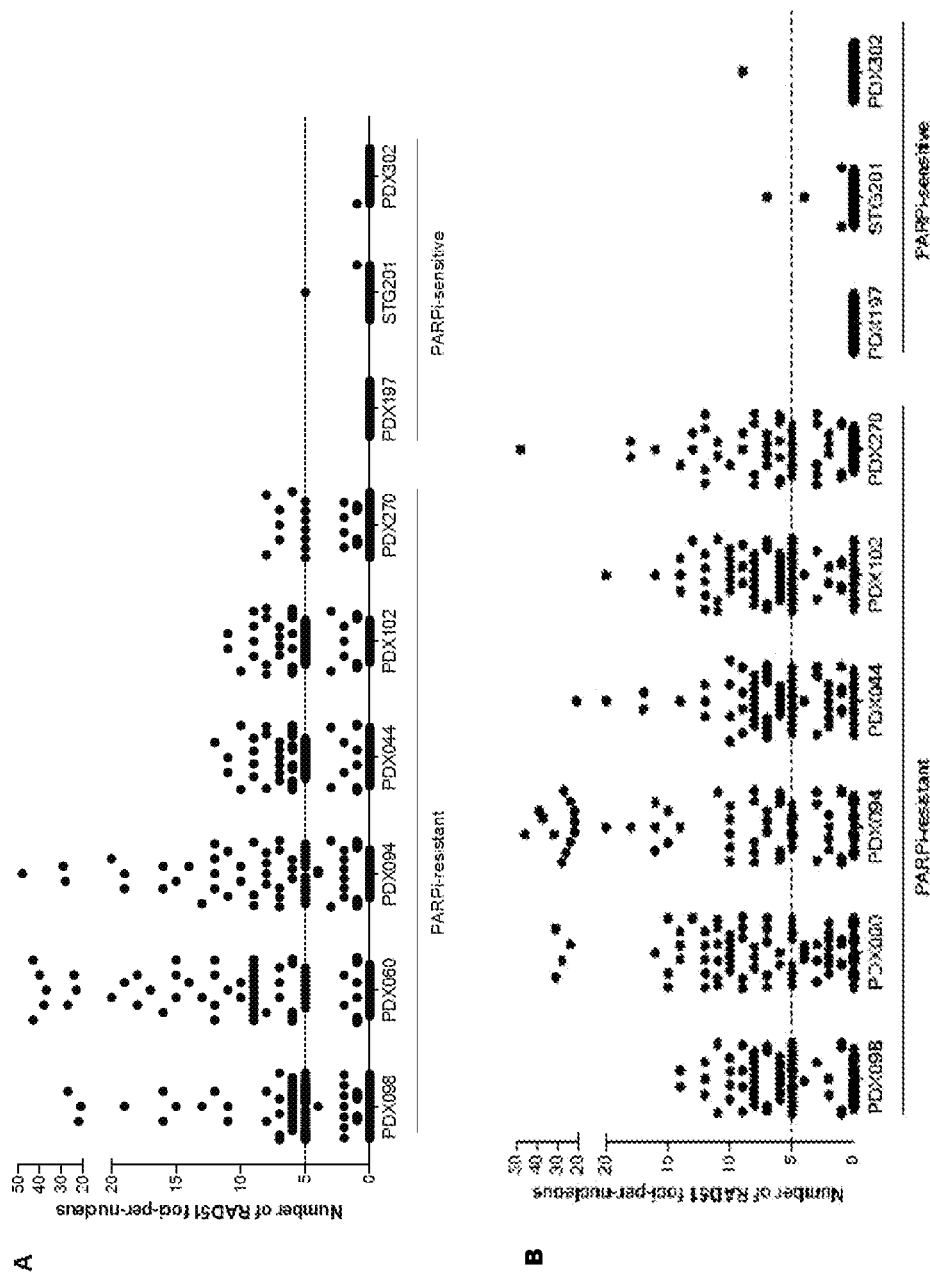
FIG. 8 shows how we established the optimal cut-off for RAD51 positivity based on the number of nuclear foci in geminin-positive cells. Scatter plots showing the number of RAD51 foci in individual geminin-positive cells (100 cells for each model were quantified) in (A) vehicle- or (B) olaparib-treated samples from nine representative PDXs models: six PARPi-resistant (PDX098, PDX060, PDX094, PDX044, PDX102 and PDX270) and three PARPi-sensitive (PDX197, STG201 and PDX302). The dashed line indicates the cut-off of 5 RAD51 foci-per-nucleus. (C) Histogram revealing that, in PARPi-sensitive tumors, 96-100% of the geminin-positive cells exhibit zero RAD51 foci. Instead, PARPi-resistant tumor cells exhibit a bimodal distribution of the frequencies of RAD51 foci per geminin-positive cell, with 35-75% of the geminin-positive cells exhibiting zero RAD51 foci and the second highest frequency peak found at 5 RAD51 foci per geminin-positive cell. In this sense, analysis of accuracy and specificity using increasing numbers of RAD51 foci per geminin-positive cell in untreated samples demonstrates that the 5 foci-per-cell cut-off is the highest RAD51 foci per geminin-positive cell threshold that provides the most accurate and specific prediction: (D) Forest plots and Odd's ratio analysis and (E) accuracy and specificity of the RAD51 score using different cut-offs from 1 to 10 foci per nucleus. This data demonstrates that several cut-offs provide accurate results and choosing 5 foci-per-nucleus (the cut-off used to generate all the data presented here) is the highest (i.e. most stringent) and still highly accurate.
Figure 8:
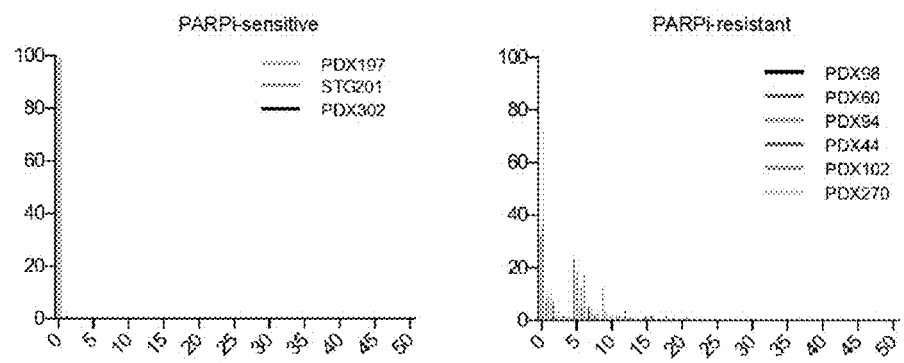
Figure 8:
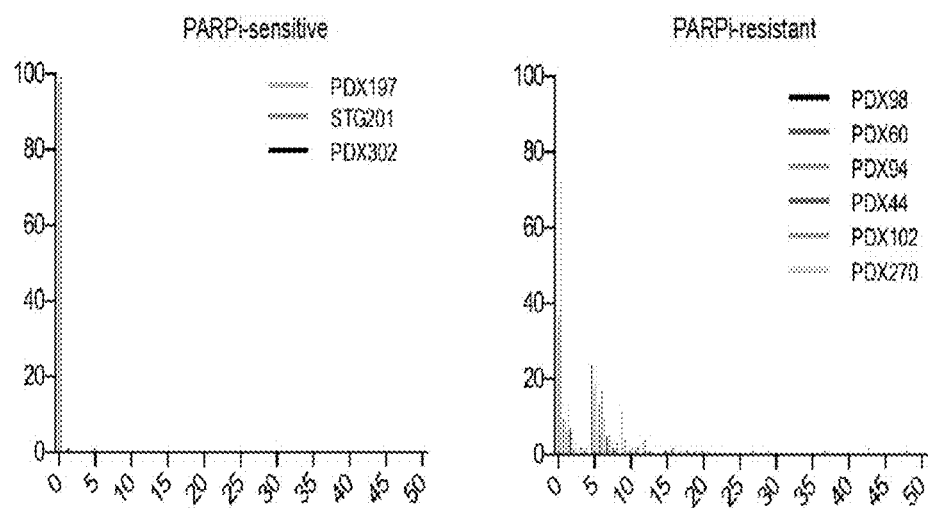
Figure 8:
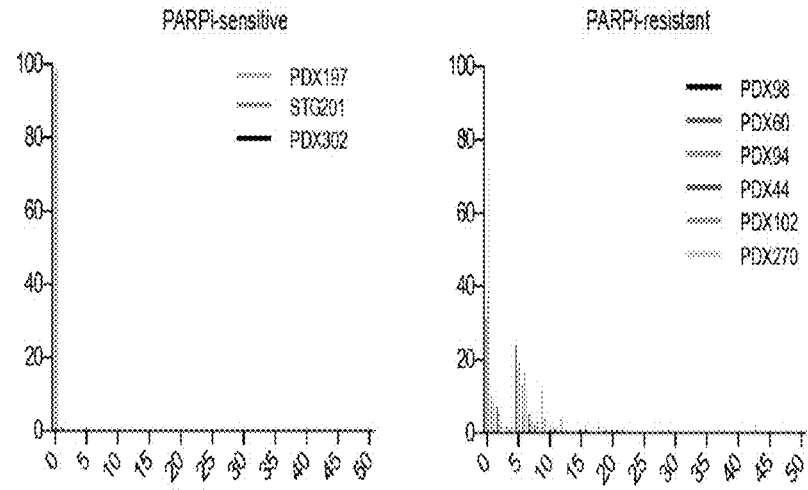

Example 8: The Optimal Cut-Off for RAD51 Positivity is Based on the Number of Nuclear Foci in Geminin-Positive Cells All the above results were obtained considering a cut-off for RAD51 positivity of at least 5 RAD51 foci per geminin-positive cell. This parameter was obtained from an in-depth analysis of absolute RAD51 foci quantification in nine representative PDX (six PARPi-resistant and three PARPi-sensitive models) as shown in FIG. 8A-B. Quantification analyses revealed that, in HRR-deficient tumors, most of the geminin-positive cells have zero RAD51 foci, while the HRR-proficient cells exhibit a bimodal distribution of the number RAD51 foci with the highest peak at 5 foci-per-cell (FIG. 8C). Regarding the prediction of PARPi response, we analysed the impact of using different thresholds in untreated samples and demonstrated that the cut-offs of 1 to 5 foci-per-cell provide the most accurate and specific predictions (FIG. 8D-E). Overall, we decided to use a cut-off of 5 foci/cell for being the highest (i.e. most stringent) and still highly accurate threshold for the analysed samples.

Figure 9:
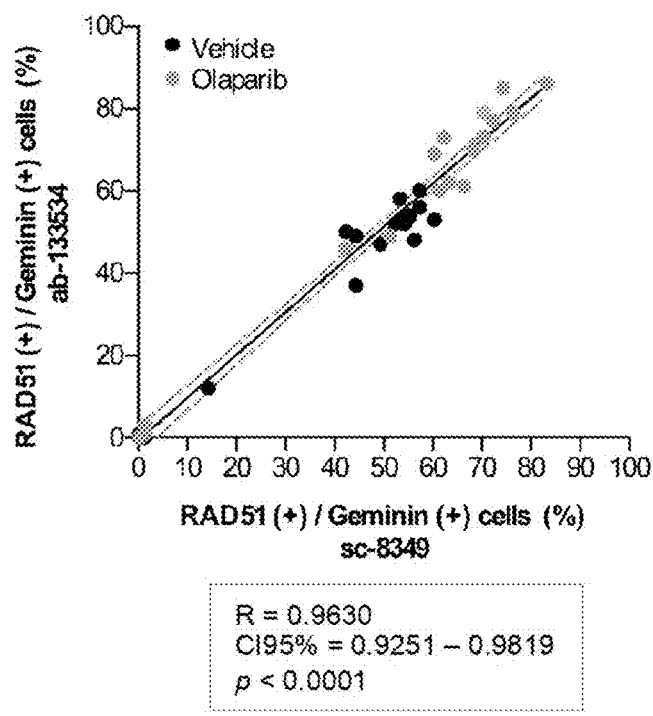
FIG. 9 shows the validation of two additional commercial anti-RAD51 antibodies and the development of the RAD51 assay by immunohistochemistry. (A) RAD51 score quantification with two different commercial antibodies against RAD51 (Santa Cruz Biotechnology 8349 and Abcam 133534) in both vehicle- and olaparib-treated PDXs. Spearman correlation analysis of the RAD51 foci quantifications with the two different antibodies demonstrates the reproducibility of the RAD51 assay. (B-C) Representative pictures showing the validation of a third anti-RAD51 antibody (Cell Signalling Technology, CST 8875) by both immunofluorescence assay (top images) and immunohistochemistry assay (bottom images). We show images from (B) HeLa cell lines (exposed to siRNA control—left- or siRNA RAD51 for knocking down its expression—right-) and (C) untreated PDXs with high, moderate (mod) and low RAD51 foci formation. These results demonstrate comparable results with both IF and IHC assays.
Figure 9:
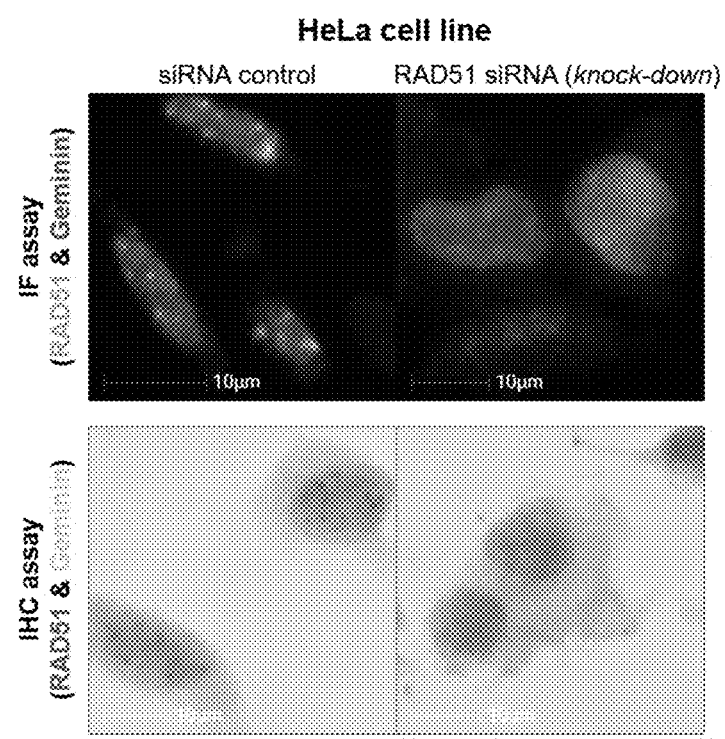
Figure 9:
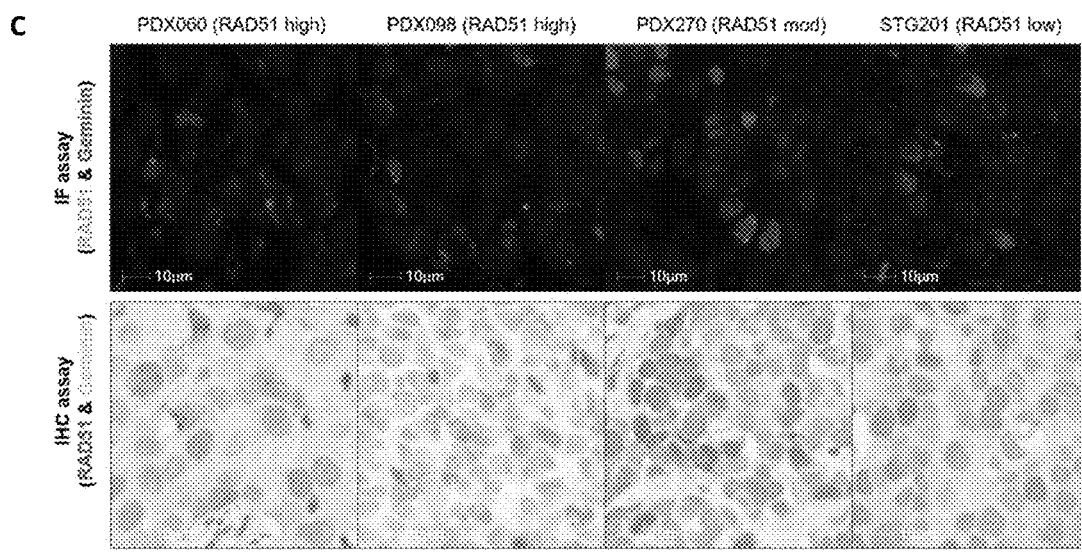
Figure 10:
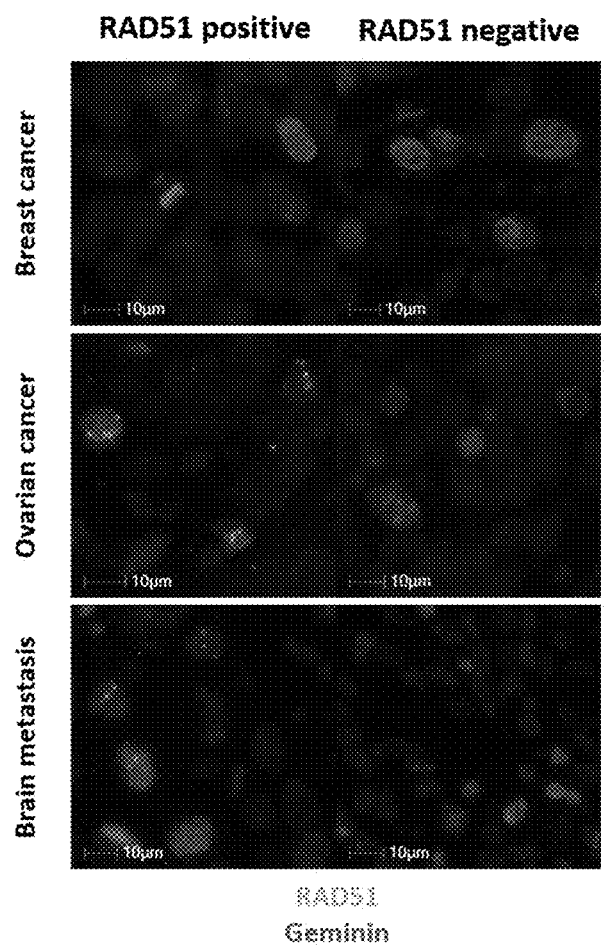
FIG. 10 shows the feasibility of the RAD51 assay across tumor types. Representative images of stained human samples from (A) breast cancer, ovarian cancer and brain metastases, as well as from (B) prostate cancer, pancreatic cancer, pediatric neuroblastoma and liver metastasis are shown. Tumor samples were stained either with (A) anti-RAD51 antibody from Cell Signalling Technology (CST 8875, in green) and Geminin (red), or (B) anti-RAD51 antibody from Abcam (ab-133534, in red) and Geminin (green). In addition, DAPI (blue) was used as a nuclear counter-stain. These pictures show that the RAD51 assay can be performed in different tumor types and can identify the presence or absence of RAD51 foci in a variety of tissues.
Figure 10:
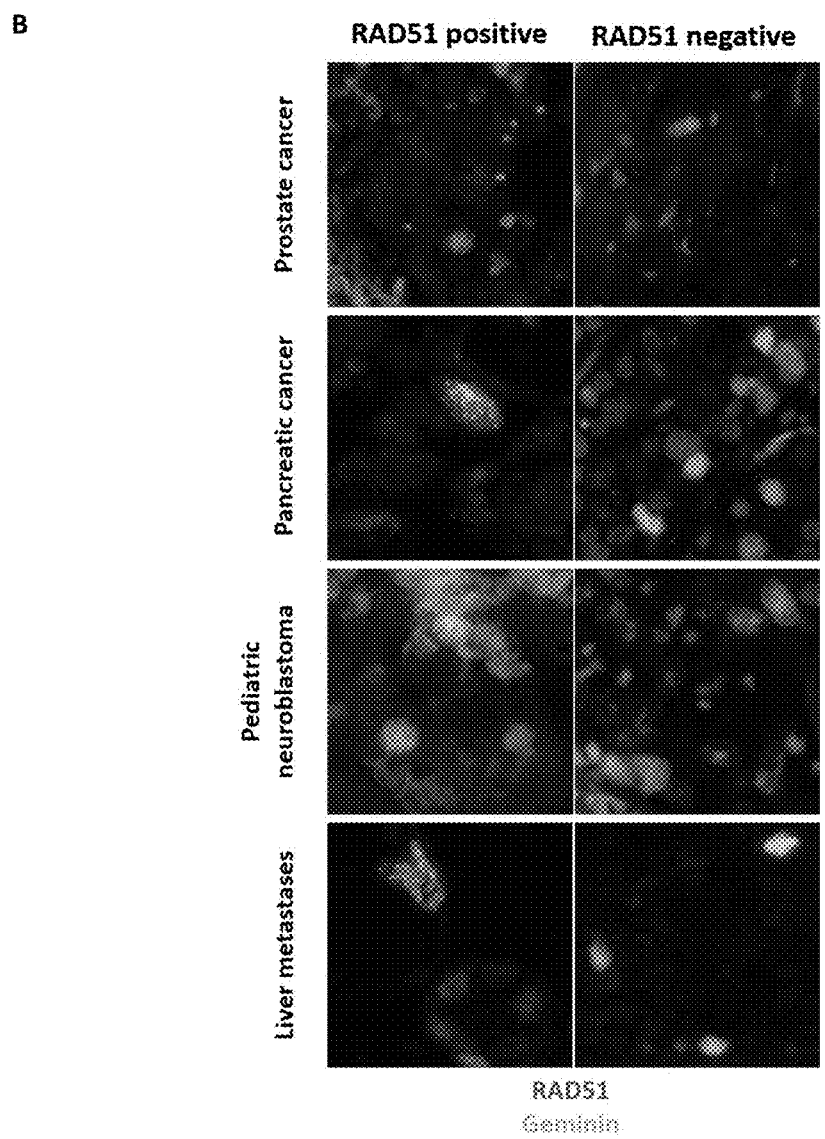

Example 9: The RAD51 Assay is Reproducible Using Other Commercial Anti-RAD51 Antibodies and Other Immune-Based Assays We validated the previous findings by quantifying the RAD51 score with another commercial antibody against RAD51 in both vehicle- and PARPi-treated tumor PDX (FIG. 9A). Similar results were also observed with a third anti-RAD51 antibody tested in RAD51 proficient/deficient cell lines (FIG. 9B) and in representative PDX (FIG. 9C). Furthermore, we developed an immunohistochemistry assay to quantify the RAD51 score and comparable results were obtained compared with the previously used immunofluorescence assay (FIG. 9B-C).

Example 10: The RAD51 Assay is Feasible in Multiple Tumor Types

So far, we have provided evidence that the RAD51 assay works in a variety of breast cancer subtypes, ovarian cancer, pancreatic cancer, prostate cancer, and metastatic sites, including skin, lymph node and bone marrow (FIG. 1-7). Finally, we also tested the performance of the RAD51 assay in other tumor types, including pediatric neuroblastoma, brain and liver metastasis. Indeed, we found RAD51 foci positive samples and RAD51 foci negative samples from a variety of tumor types, suggesting the potential expanded use of the RAD51 assay across tumors.

In sum, these results demonstrate that the RAD51 score is a robust and highly accurate biomarker of HRR functionality and response to anti-cancer therapies in distinct tumor types.

The information claimed is:

1. A method for the treatment of a cancer in a subject in need thereof, the method comprising the administration to said subject of a therapeutically effective amount of a PARP inhibitor agent, wherein the subject has been identified as responder to said PARP inhibitor agent by a method for predicting the response of a subject diagnosed with cancer to the PARP inhibitor agent which comprises:
   i) determining the level of cells with RAD51 foci in a sample containing tumor cells isolated from said subject wherein the subject has not received, within 24 hours prior to the isolation of the sample, a chemotherapy selected from the group consisting of AC, FEC, ECF and navelbine/epirubicin, and
   wherein the sample has not been treated with a method that induces DNA damage before determining the level of cells with RAD51 foci, and
   ii) comparing the level obtained in step i) with a reference value, wherein:
   a level of cells with RAD51 foci lower than said reference value indicates that the subject is predicted to respond to the PARP inhibitor agent, or
   a level of cells with RAD51 foci equal or higher than said reference value, indicates that the subject is predicted not to respond to the PARP inhibitor agent.

2. The method according to claim 1 wherein the PARP inhibitor agent is selected from the list consisting of olaparib, veliparib, niraparib, talazoparib, rucaparib, CEP-8983, E7016, BGB-290, and 3-aminobenzamide.

3. The method according to claim 1 wherein the level of cells with RAD51 foci in the sample is determined as the relative level of cells with RAD51 foci with respect to:
   the number of tumor cells in the sample,
   the number of cells in the sample that are proliferating,
   the number of cells in the sample that show DNA damage, and
   the number of cells in the sample that are proliferating and that show DNA damage.

4. The method according to claim 3 wherein the number of cells in the sample that are proliferating is determined by determining the expression of a protein selected from the list consisting of Geminin, KI-67, Proliferating cell nuclear antigen, Cyclin A2, and/or wherein the number of cells in the sample that show double strand DNA breaks is determined by the expression in the nucleus of a protein selected from the list consisting of γH2AX, replication protein A (pRPA), p53 Binding protein 1 (53BP1), double-strand break repair protein (MRE11).

5. The method according to claim 4 wherein the number of cells in the sample that are proliferating is determined by determining the expression of Geminin, and wherein the number of cells in the sample that show double strand DNA breaks is determined by the expression in the nucleus of γH2AX.

6. The method according to claim 1 wherein the subject from whom the sample has been isolated has received an anti-cancer treatment before the isolation of the sample, wherein the anti-cancer treatment is different from a chemotherapy selected from the group consisting of AC, FEC, ECF and navelbine/epirubicin if the patient has received the anti-cancer treatment within 24 hours prior to the isolation of the sample.

7. The method according to claim 3, wherein the DNA damage is double strand DNA breaks.

\* \* \* \* \*